(12) United States Patent
Keri et al.

(10) Patent No.: US 7,262,218 B2
(45) Date of Patent: *Aug. 28, 2007

(54) FORMS OF PRAVASTATIN SODIUM

(75) Inventors: Vilmos Keri, Debrecen (HU); Csaba Szabo, Debrecen (HU); Edit Nagyne Arvai, Debrecen (HU); Judith Aronhime, Rechovot (IL)

(73) Assignee: Teva Gyogyszergyar Zartkoruen Mukodo Reszvenytarsasag (HU)

( * ) Notice: Subject to any disclaimer, the term of this patent is extended or adjusted under 35 U.S.C. 154(b) by 0 days.

This patent is subject to a terminal disclaimer.

(21) Appl. No.: 11/200,794

(22) Filed: Aug. 9, 2005

(65) Prior Publication Data

US 2005/0288370 A1  Dec. 29, 2005

Related U.S. Application Data

(63) Continuation of application No. 09/736,796, filed on Dec. 14, 2000, now Pat. No. 7,001,919.

(60) Provisional application No. 60/190,649, filed on Mar. 20, 2000, provisional application No. 60/170,685, filed on Dec. 14, 1999.

(51) Int. Cl.
 *A61K 31/225* (2006.01)
(52) U.S. Cl. .................................................. 514/548
(58) Field of Classification Search ................ None
See application file for complete search history.

(56) References Cited

U.S. PATENT DOCUMENTS

| | | | |
|---|---|---|---|
| 4,319,039 A | 3/1982 | Albers-Schonberg | |
| 4,346,227 A | 8/1982 | Terahara et al. | |
| 4,410,629 A | 10/1983 | Terahara et al. | |
| 4,857,522 A | 8/1989 | DiPietro et al. | |
| 4,857,547 A | 8/1989 | Hoffman et al. | |
| 5,099,035 A | 3/1992 | Saunders et al. | |
| 5,140,012 A | 8/1992 | McGovern et al. | |
| 5,153,124 A | 10/1992 | Furuya et al. | |
| 5,157,025 A | 10/1992 | Aberg et al. | |
| 5,180,589 A | 1/1993 | Joshi et al. | |
| 5,202,029 A | 4/1993 | Haytko et al. | |
| 5,616,595 A | 4/1997 | Chu et al. | |
| 5,712,130 A | 1/1998 | Hajko et al. | |
| 5,883,109 A | 3/1999 | Gregg et al. | |
| 5,942,423 A | 8/1999 | Demain et al. | |
| 6,444,452 B1 | 9/2002 | Keri et al. | |
| 6,682,913 B1 | 1/2004 | Jekkel et al. | |
| 6,695,969 B1 | 2/2004 | Grahek et al. | |
| 6,696,599 B2 | 2/2004 | Jekkel et al. | |
| 6,750,366 B2 | 6/2004 | Jekkel et al. | |
| 7,001,919 B2 * | 2/2006 | Keri et al. .................. 514/548 |
| 2004/0039225 A1 | 2/2004 | Jekkel et al. | |

FOREIGN PATENT DOCUMENTS

| | | |
|---|---|---|
| EP | 0 215 665 | 3/1987 |
| EP | 0 605 230 | 7/1994 |
| EP | 0 671 170 | 9/1995 |
| WO | WO92/16276 | 10/1992 |
| WO | WO98/37220 | 8/1998 |
| WO | WO98/45410 | 10/1998 |
| WO | WO99/10499 | 3/1999 |
| WO | WO99/42601 | 8/1999 |
| WO | WO 00/17182 | 3/2000 |
| WO | WO 0033821 A1 * | 6/2000 |
| WO | WO 00/46175 | 8/2000 |
| WO | WO 01/03647 | 1/2001 |
| WO | WO 01/10813 | 2/2001 |
| WO | WO 2002/030415 | 4/2002 |

OTHER PUBLICATIONS

Budavari, et al. The Merck Index. 1989. Merck and Co., Inc., p. 1222.
T. Koga et al., "Tissue-selective inhibition of cholesterol synthesis in vivo by pravastatin sodium, a 3-hydroxy-3-methyglutaryl coenzyme A reductase inhibitor", *Biochimica et Biophysica Acta*, vol. 1045, No. 1, pp. 115-120, Jun. 28, 1990.
Serajuddin et al. "Relative Lipophilicities, Solubilities, and Structure-Pharmacological Considerations of 3-Hydroxy-3-Methylglutaryl-Coenzyme A (HMG-CoA) Reductase Inhibitors Pravastatin, Lovastatin, Mevastatin, and Simvastatin", *Journal of Pharmaceutical Sciences*, vol. 80, No. 9, pp. 830-834, Sep. 1991.
McMaster, Chem 2O06 Lab Manual, 1997, www.chemistry.mcmaster.ca/~chem2o6/labmanual/expt1/exp1b-i.html, pp. 1-9.

* cited by examiner

*Primary Examiner*—Paul A. Zucker
(74) *Attorney, Agent, or Firm*—Kenyon & Kenyon LLP

(57) ABSTRACT

New polymorphic forms of pravastatin sodium are provided. Each of the new forms is selectively obtained by crystallization from different solvent systems, each solvent system having a protic component, and by controlling the rate of crystallization through temperature. The new polymorphic forms are suitable for use as active substances of pharmaceutical dosage forms for reduction of serum cholesterol levels in the bloodstream.

5 Claims, 19 Drawing Sheets

FORMS OF PRAVASTATIN SODIUM

RELATED APPLICATION

This application is a continuation of U.S. patent application Ser. No. 09/736,796, filed Dec. 14, 2000, which issued as U.S. Pat. No. 7,001,919 on Feb. 21, 2006, which claims the benefit under 35 U.S.C. § 1.119(e) of U.S. Provisional Patent Application No. 60/170,685, filed Dec. 14, 1999 and U.S. Provisional Patent Application No. 60/190,649, filed Mar. 20, 2000, the contents of all of which are incorporated herein by reference.

FIELD OF THE INVENTION

The present invention relates to statins, and more particularly to novel polymorphic forms of pravastatin sodium.

BACKGROUND OF THE INVENTION

Pravastatin is a member of the class of pharmaceutical compounds called statins. Statins currently are the most effective treatment for lowering serum cholesterol levels in patients with atherosclerosis and hypercholesteremia. Pravastatin is the common medicinal name of the chemical compound [1S-[1α(β*,δ*)2α,6α,8β(R*),8aα]]-1,2,6,7,8,8a-hexahydro-β,δ,6-trihydroxy-2-methyl-8-(2-methyl-1-oxobutoxy)-1-naphthalene-heptanoic acid. (CAS Registry No. 81093-37-0) The molecular structure of pravastatin is represented by Formula (I). "Pravastatin sodium" is defined as the monosodium salt of pravastatin, whether hydrated or anhydrous, solvated or unsolvated.

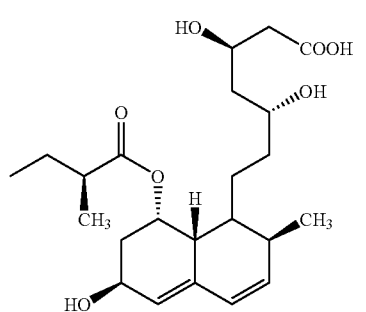

(I)

According to U.S. Pat. No. 4,346,227, incorporated herein by reference, pravastatin is reported as having been first isolated as a metabolite of compactin by M. Tanaka et al. during a study of compactin metabolism. The '227 patent discloses the isolation of pravastatin in its lactone form, as the methyl ester of the free carboxylic acid and as the monosodium salt of the free carboxylic acid ("pravastatin sodium"). Pravastatin sodium was analyzed by nuclear magnetic resonance spectroscopy, infrared ("IR") spectroscopy, ultraviolet spectroscopy and thin layer chromatography. Pravastatin sodium was analyzed in solid form by IR spectroscopy using the conventional technique of co-mixing with potassium bromide ("KBr") and then compressing to form a KBr window or pellet. The IR spectrum of the pravastatin sodium obtained by absorption bands at 3400, 2900, 1725, 1580 cm$^{-1}$. All other spectral measurements are repeated on pravastatin sodium in solution.

The present invention relates to new crystal forms of pravastatin sodium and compositions containing them. Polymorphism is the property of some molecules and molecular complexes to assume more than one crystalline form in the solid state. A single molecule may give rise to a variety of crystal forms (also called "polymorphs") having distinct physical properties. The existence of more than one crystal form can be determined in a laboratory by comparison of the angles at which X-ray radiation reflected from the forms undergoes constructive interference and by comparing the absorptions of incident infrared radiation at different wavelengths. The former technique is known as X-ray diffraction spectroscopy and the angles at which constructive interference occurs are known as reflections.

The differences in the physical properties of polymorphs result from the orientation and intermolecular interactions of adjacent molecules (complexes) in the bulk solid. Accordingly, polymorphs are distinct solids sharing the same molecular formula yet having distinct advantageous and/or disadvantageous physical properties compared to other forms in the polymorph family.

One of the most important physical properties of a polymorphic pharmaceutical compound is the solubility of each of its forms in aqueous solution, particularly the solubility in gastric juices of a patient. Other important properties relate to the ease of processing the form into pharmaceutical dosages, such as the tendency of a powdered or granulated form to flow and the surface properties that determine whether crystals of the form will adhere to each other when compacted into a tablet.

SUMMARY OF THE INVENTION

The present invention is directed to new polymorphic forms of pravastatin sodium. These forms are designated Form A, Form B, Form C, Form D, Form E, Form F, Form G, Form H, Form H1, Form I, Form J, Form K and Form L. The invention is also directed to methods of making each of the pravastatin sodium polymorphs.

DETAILED DESCRIPTION OF THE INVENTION

We have discovered new polymorphic forms of pravastatin sodium that can be distinguished from the known amorphous pravastatin sodium and from each other by their powder X-ray reflections and their infrared absorption spectra.

All powder X-ray diffraction patterns were obtained by methods known in the art using a Philips X-ray powder diffractometer, with goniometer model 1050/70, at scanning speed of 2° min.$^{-1}$. Copper radiation of $\lambda$=1.5418 Å was used.

The infrared spectrum was obtained in a Nujol mull using a Perkin Elmer Paragon 1000 FT-IR spectrometer at 4 cm$^{-1}$ resolution with 16 scans. The characteristic infrared absorption bands of the novel forms of pravastatin sodium will not necessarily be observed in the IR spectrum of a sample that has been dissolved, as for example in chloroform or carbon tetrachloride, for IR analysis. That is: some IR bands may be characteristic of pravastatin in the solid state; others are characteristic of pravastatin sodium whether in the solid or solution phase.

Pravastatin crystal forms show DSC curves with multiple endothermic and exothermic events due to water desorption and phase transitions. The melting peak observed in all forms except form B is in the range of about 174-176° C. Form B has a melting point at about 187° C.

Pravastatin crystal forms exhibit hygroscopic behavior. The water uptake at 80% relative humidity after 1 week was up to about 15%. After exposure at 100% relative humidity, all the forms of pravastatin sodium transform to Form C with about 30% relative humidity. It was also found that all the crystal forms, except Form B, were transformed to Form D by heating at 120° C. for 2 hours.

Characteristics of Pravastatin Sodium Polymorphs

Figure 1:
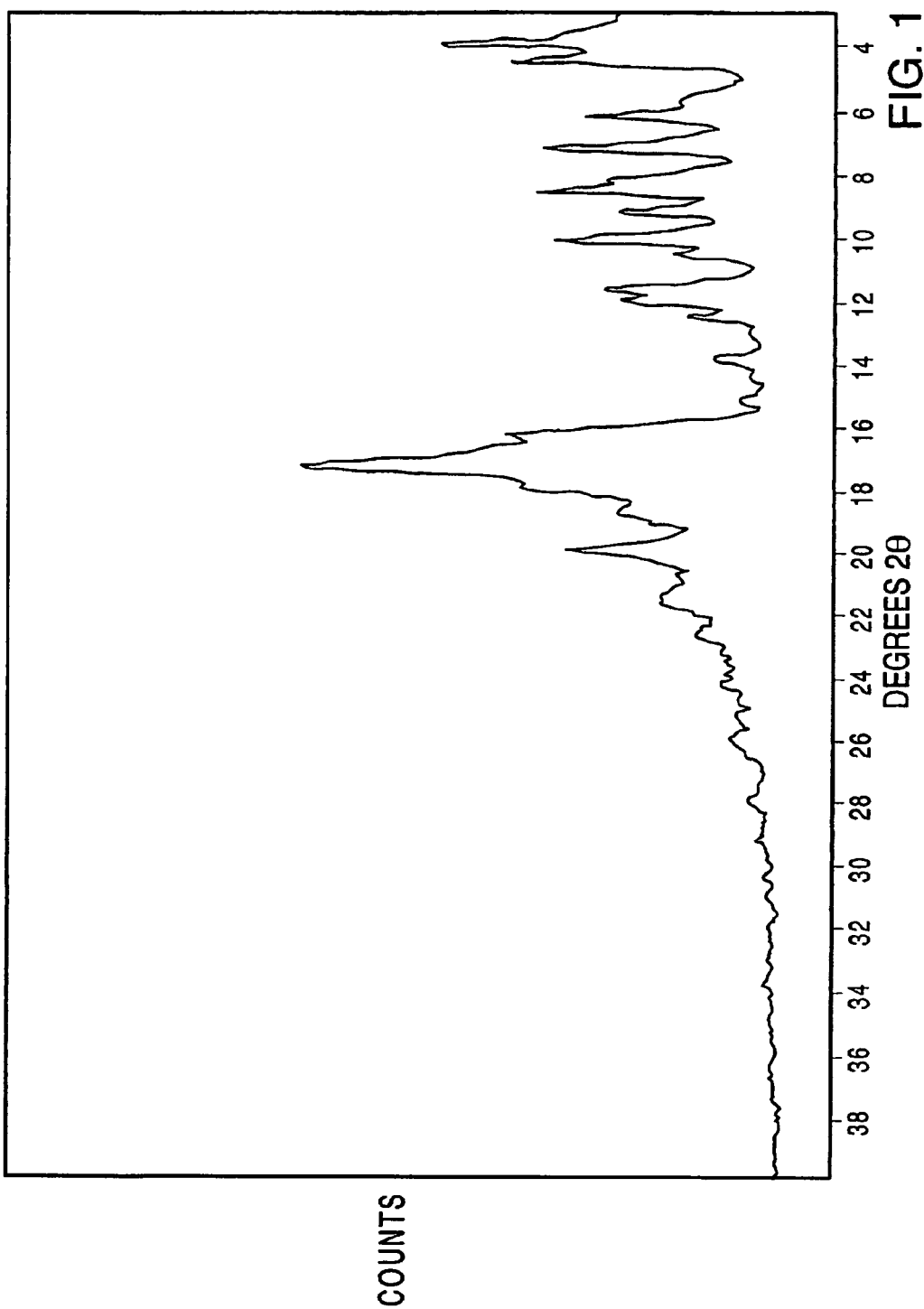
FIG. 1 is a characteristic powder X-ray diffraction pattern of pravastatin sodium Form A.
Figure 2:
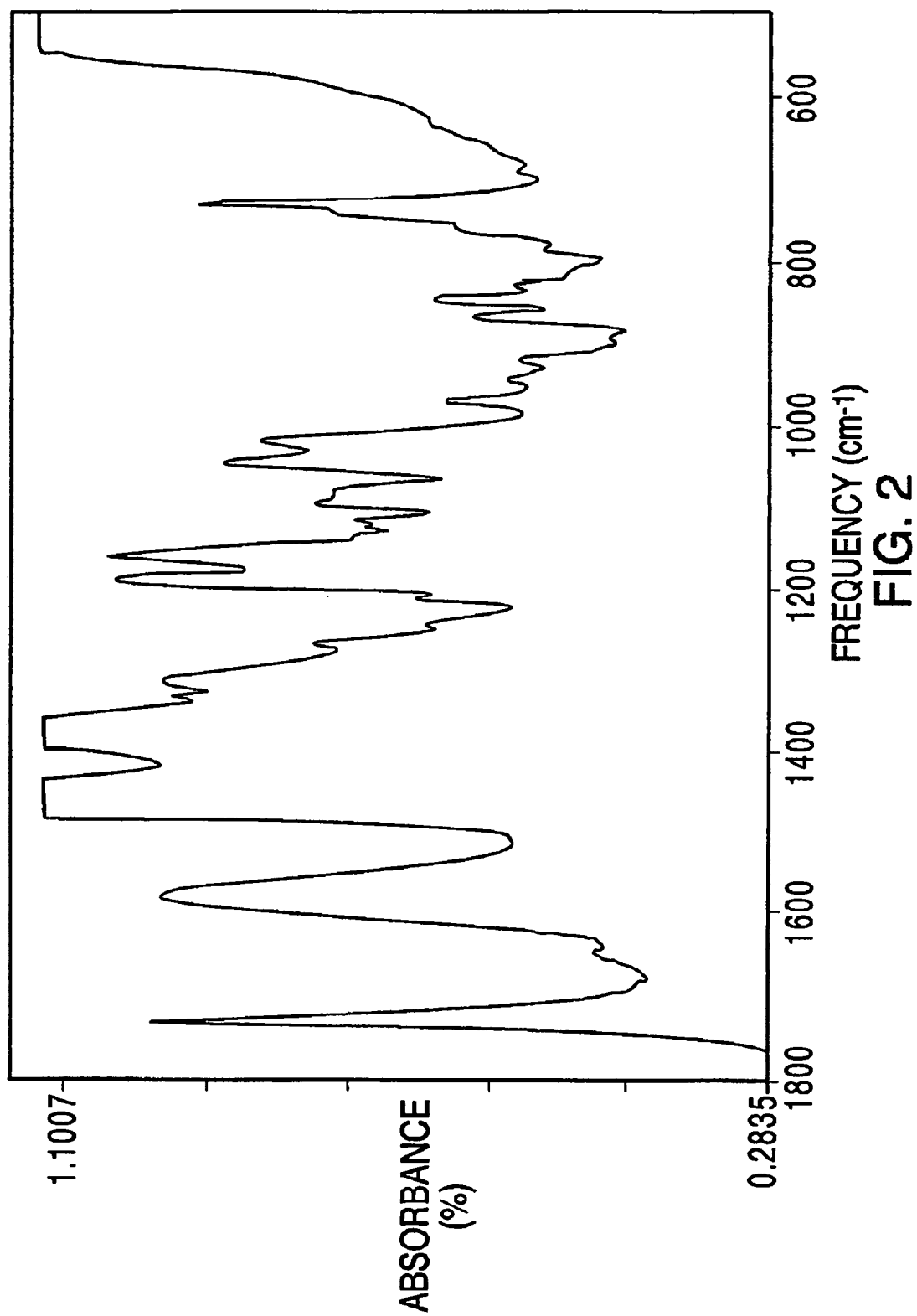
FIG. 2 is a characteristic infrared absorption spectrum of pravastatin sodium Form A.

Pravastatin sodium Form A is characterized by reflections in the powder X-ray diffraction pattern at 3.9, 4.5, 6.2, 7.2, 8.6, 9.2, 10.0, 11.6, 12.0, 17.0 and 20.0±0.2 degrees, detected at reflection angle 2θ. The diffraction pattern is reproduced in FIG. 1. Of these, the reflections at 3.9, 4.5, 6.2, and 7.2±0.2 degrees are especially characteristic. Form A may also be distinguished by its infrared absorption spectrum which is shown in FIG. 2 obtained in a Nujol mull. Form A has characteristic; absorption bands at 686, 826, 842, 864, 917, 939, 965, 1013, 1040, 1092, 1111, 1156, 1184, 1265, 1310, 1330, 1576 and 1726,±2 cm$^{-1}$.

Figure 3:
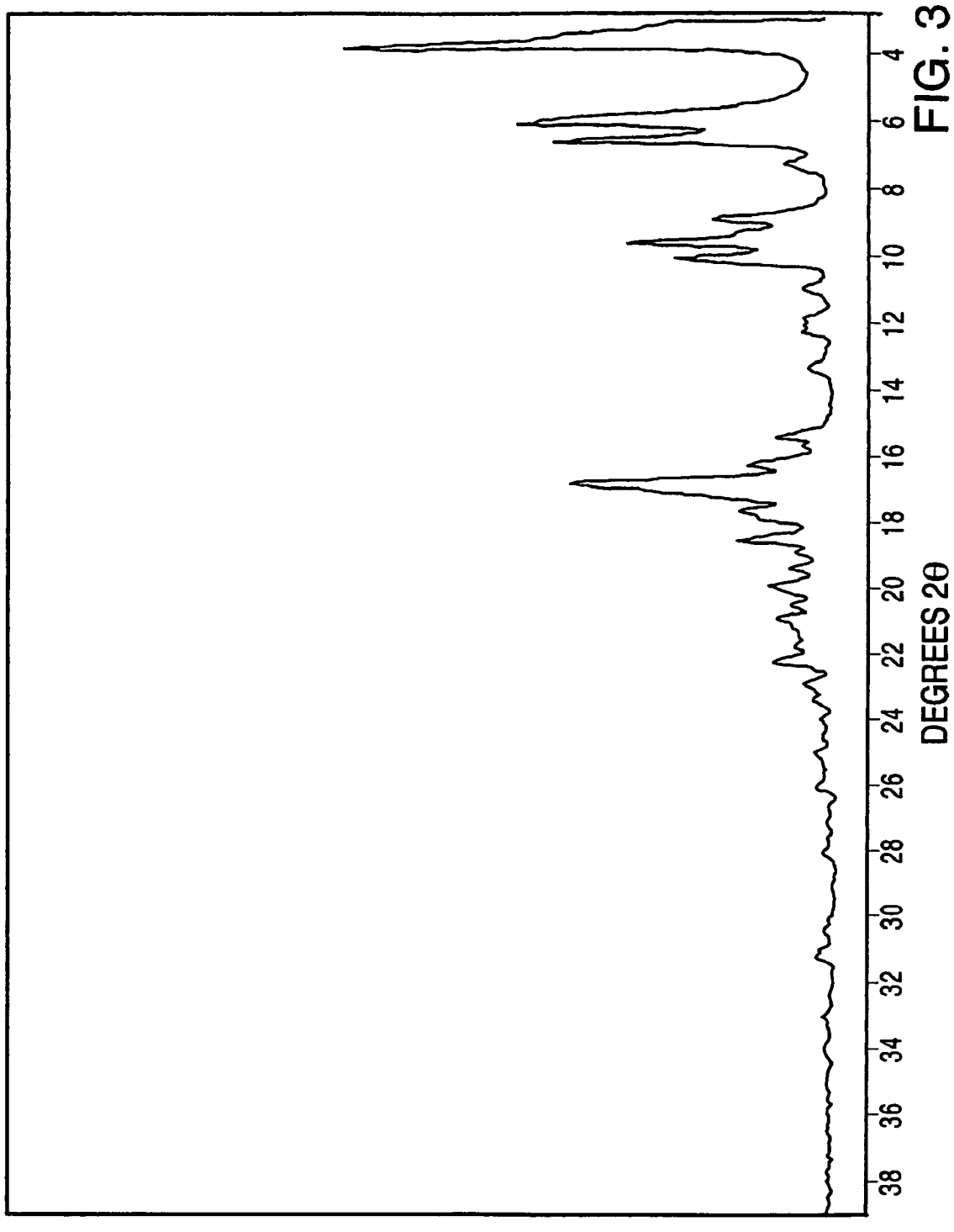
FIG. 3 is a characteristic powder X-ray diffraction pattern of pravastatin sodium Form B.
Figure 4:
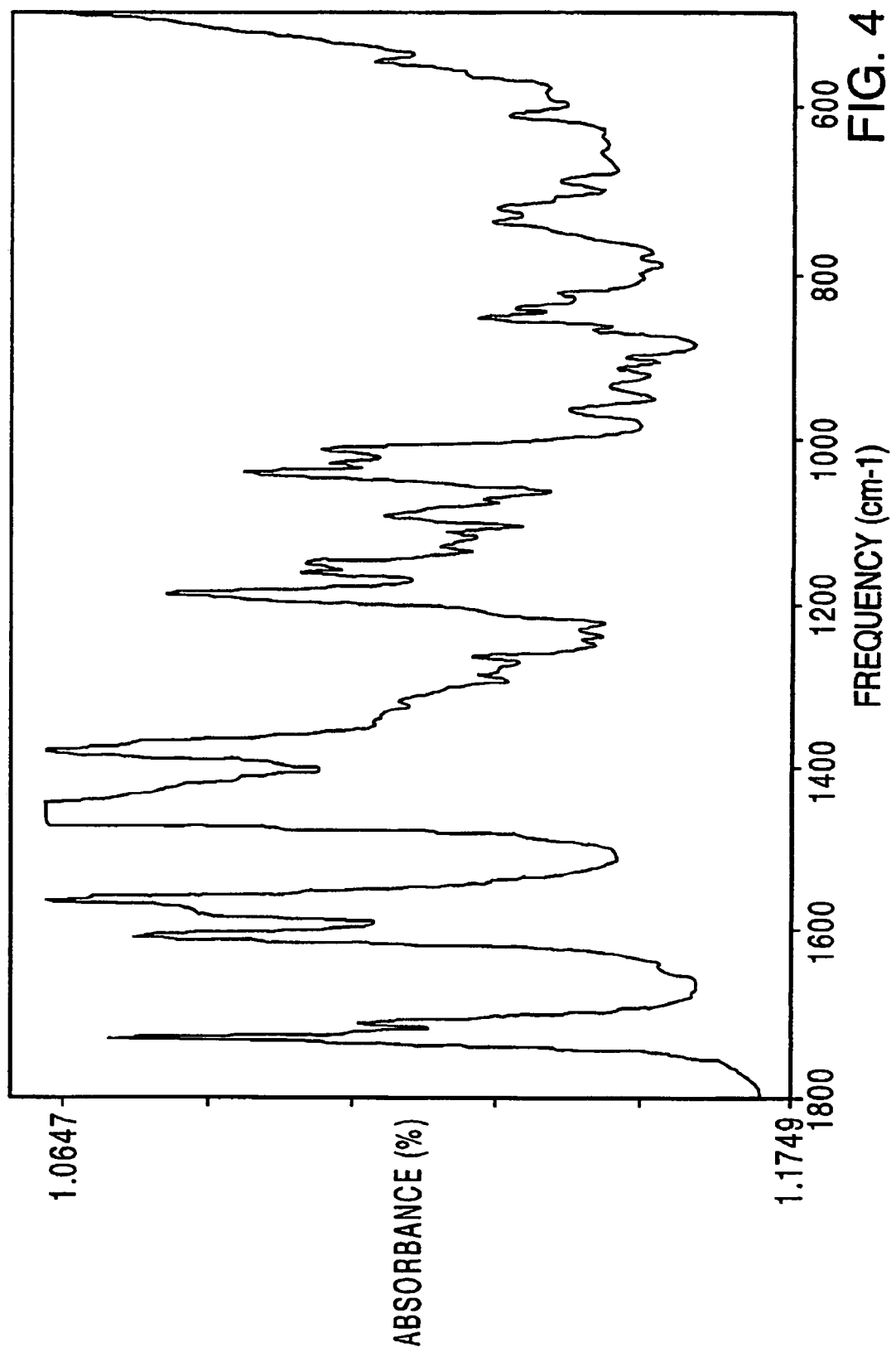
FIG. 4 is a characteristic infrared absorption spectrum of pravastatin sodium Form B.

Pravastatin sodium Form B is distinguished by reflections in the powder X-ray diffraction pattern that are observed at 3.6, 6.1, 6.6, 9.0, 9.6, 10.1, 16.4, 16.8 and 18.6±0.2 degrees detected at the reflection angle 2θ. The diffraction pattern is reproduced in FIG. 3. The reflections at 3.6, 6.1, 6.6, 9.0, 9.6, 10.1 and 18.6±0.2 degrees are the most intense and in that sense the most characteristic, the reflections at 3.6, 6.1 and 6.6±0.2 degrees being the most intense of all. Form B may further be distinguished by its IR spectrum, provided as FIG. 4, obtained from a Nujol mull. Absorption bands are observed at 614, 692, 739, 824, 842, 854, 868, 901, 914, 936, 965, 1011, 1028, 1039, 1072, 1091, 1111, 1129, 1149, 1161, 1185, 1232, 1245, 1318, 1563, 1606, 1711 and 1730±2 cm$^{-1}$.

Figure 5:
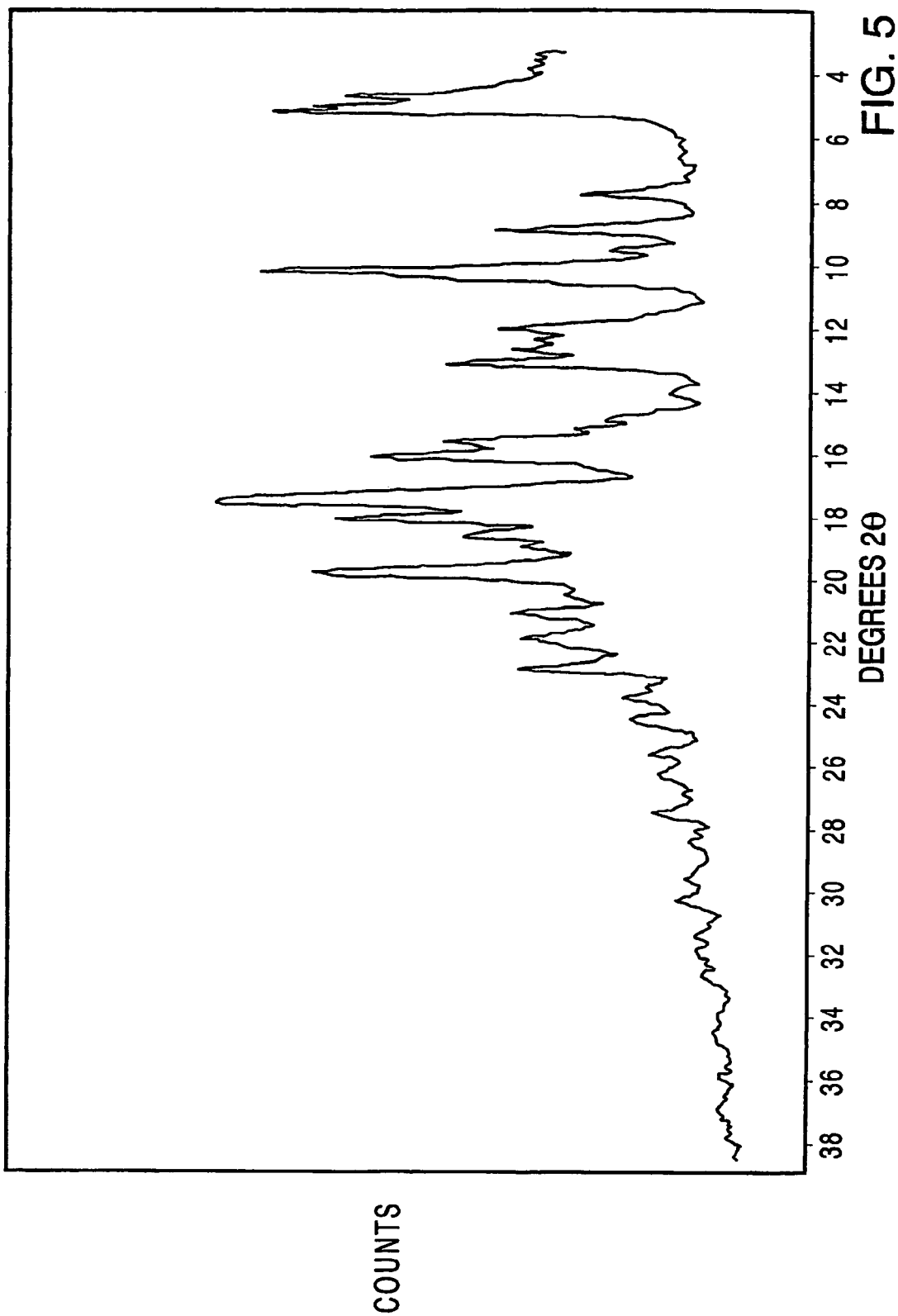
FIG. 5 is a characteristic powder X-ray diffraction pattern of pravastatin sodium Form C.
Figure 6:
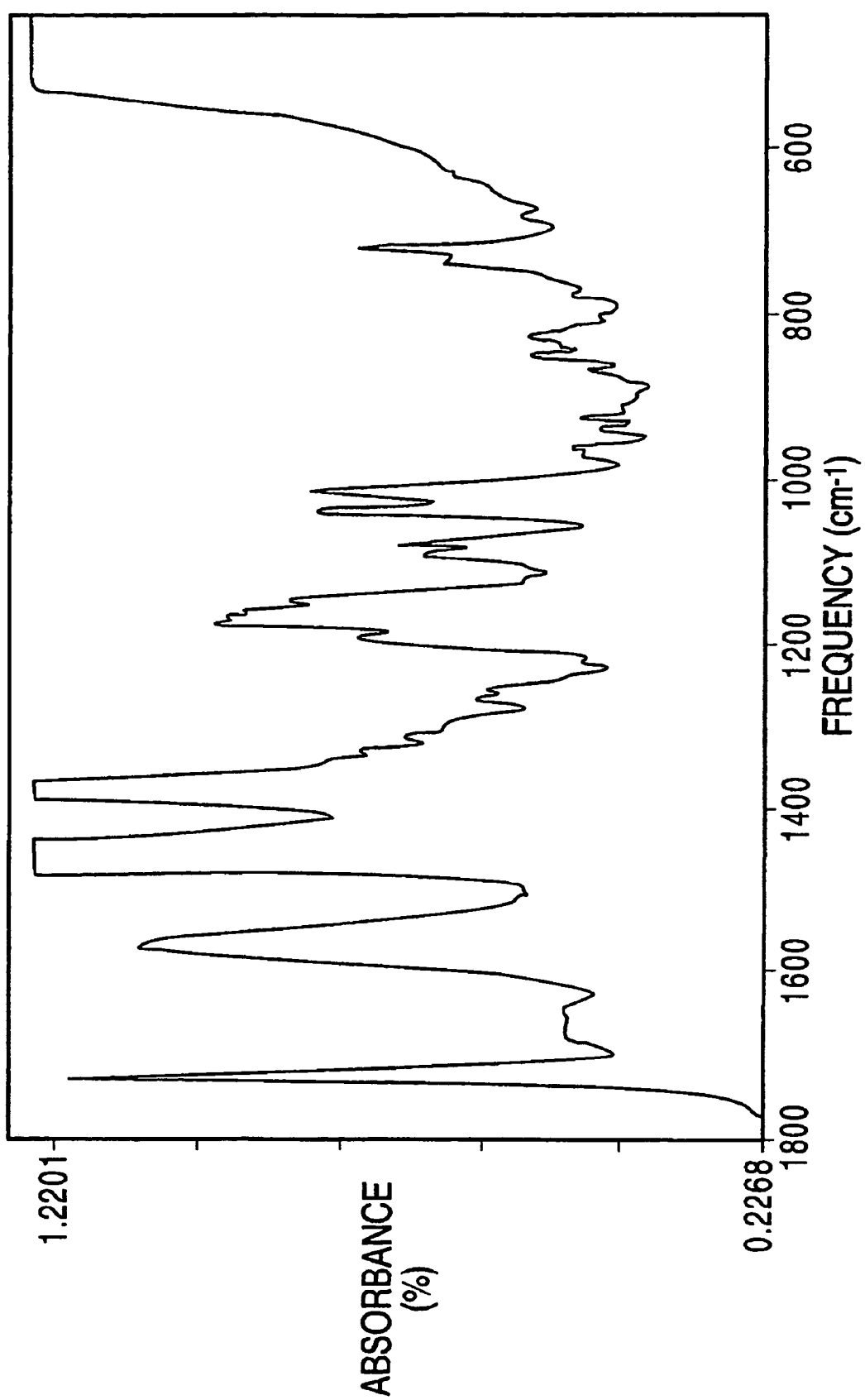
FIG. 6 is a characteristic infrared absorption spectrum of pravastatin sodium Form C.

Pravastatin sodium Form C may be distinguished by reflections in the powder X-ray diffraction pattern that are observed at about 4.8, 7.6, 8.6, 10.0, 11.8, 12.4, 13.0, 15.5, 16.0, 17.4, 17.9, 18.4, 19.7, 21.0, 21.8 and 22.8±0.2 degrees, detected at reflection angle 2θ. The reflections observed at 4.8, 7.6, 8.7, 10.0, 13.0, 16.0, 17.4 and 19.7±0.2 degrees are characteristic and, of these, the reflections at 4.8, 10.0, 13.0, 16.0 and 17.4±0.2 degrees are especially characteristic. The diffraction pattern is reproduced in FIG. 5. Form C may further be distinguished by its IR spectrum, provided as FIG. 6, obtained from a Nujol mull. Absorption bands of pravastatin sodium Form C are observed at 742, 829, 851, 870, 926, 940, 964, 1013, 1038, 1078, 1090, 1146, 1166, 1174, 1194, 1257, 1268, 1313, 1328, 1567 and 1728±2 cm$^{-1}$.

Figure 7:
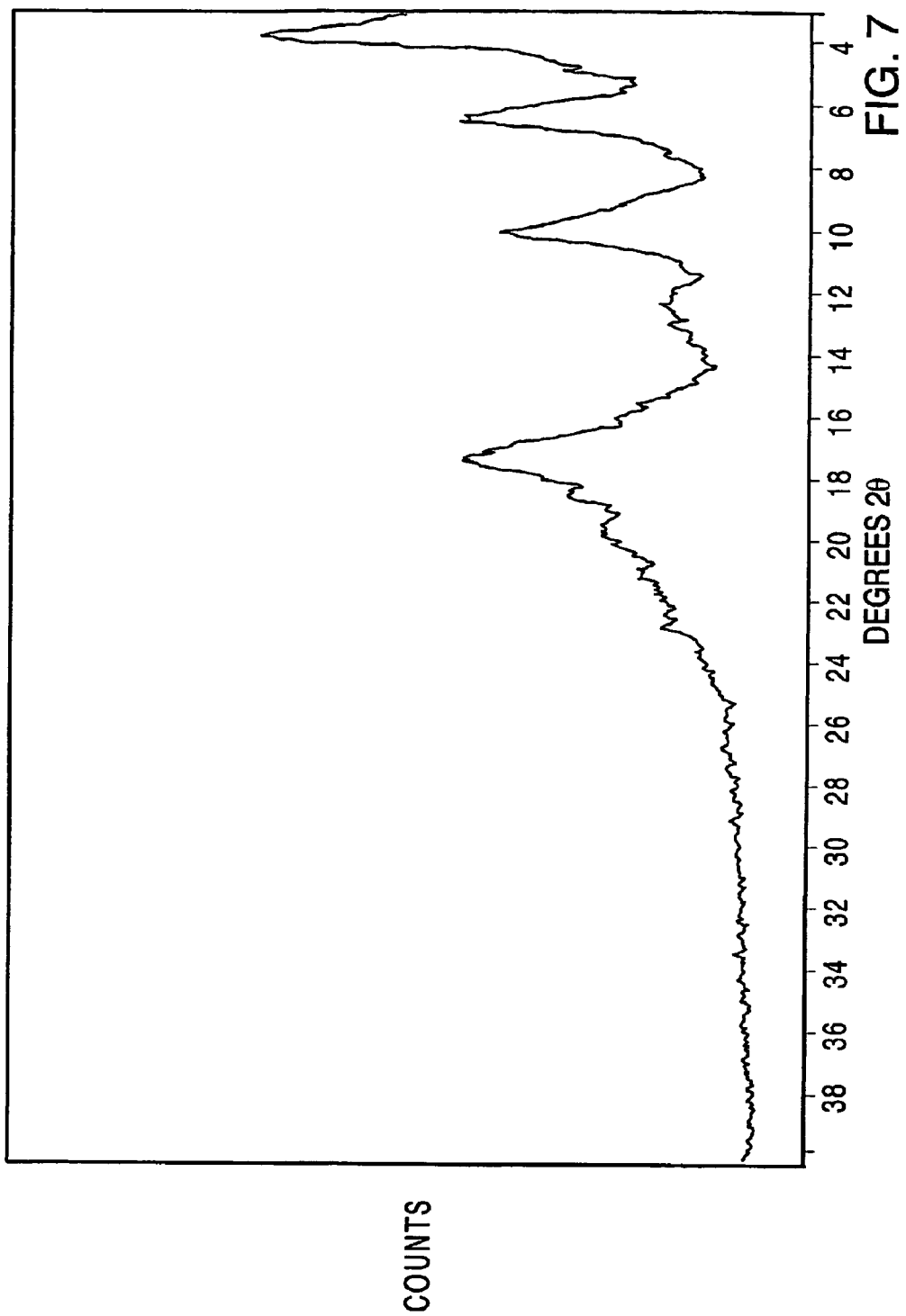
FIG. 7 is a characteristic powder X-ray diffraction pattern of pravastatin sodium Form D.
Figure 8:
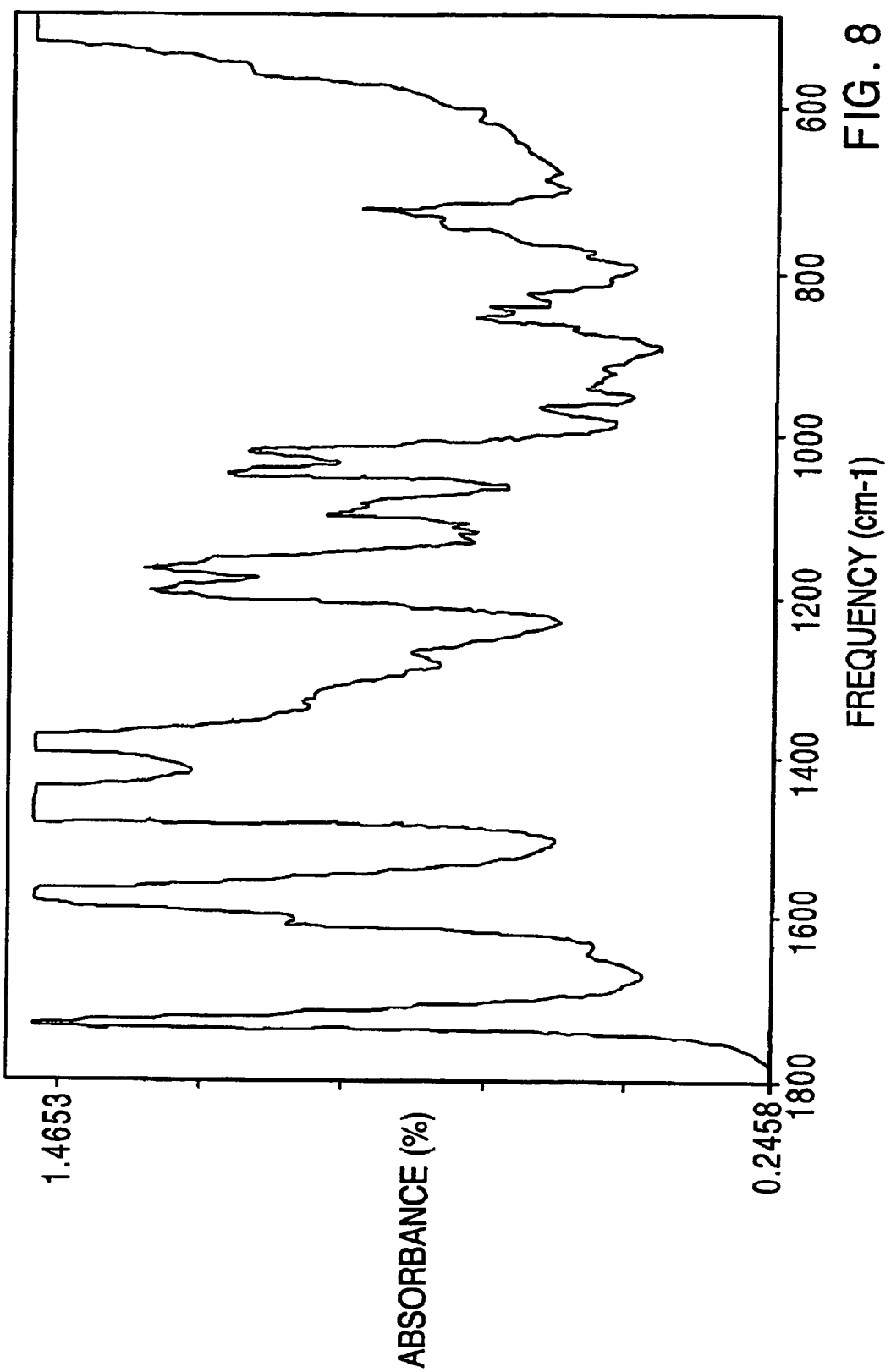
FIG. 8 is a characteristic infrared absorption spectrum of pravastatin sodium Form D.

Pravastatin sodium Form D may be distinguished from the other forms of crystalline and amorphous pravastatin sodium by reflections in the powder X-ray diffraction pattern that are observed at 3.6, 6.3, 9.8 and 17.1±0.2 degrees, detected at reflection angle 2θ. The diffraction pattern is reproduced in FIG. 7. Form D may further be distinguished by its IR spectrum, provided as FIG. 8, obtained from a KBr window using the same equipment and methodology as was used to obtain the IR spectrum of Form A. Characteristic absorption bands of pravastatin sodium Form D are observed at 824, 843, 854, 914, 939, 965, 1013, 1041, 1079, 1091, 1157, 1186, 1266, 1566, 1606 and 1728±2 cm$^{-1}$.

Figure 9:
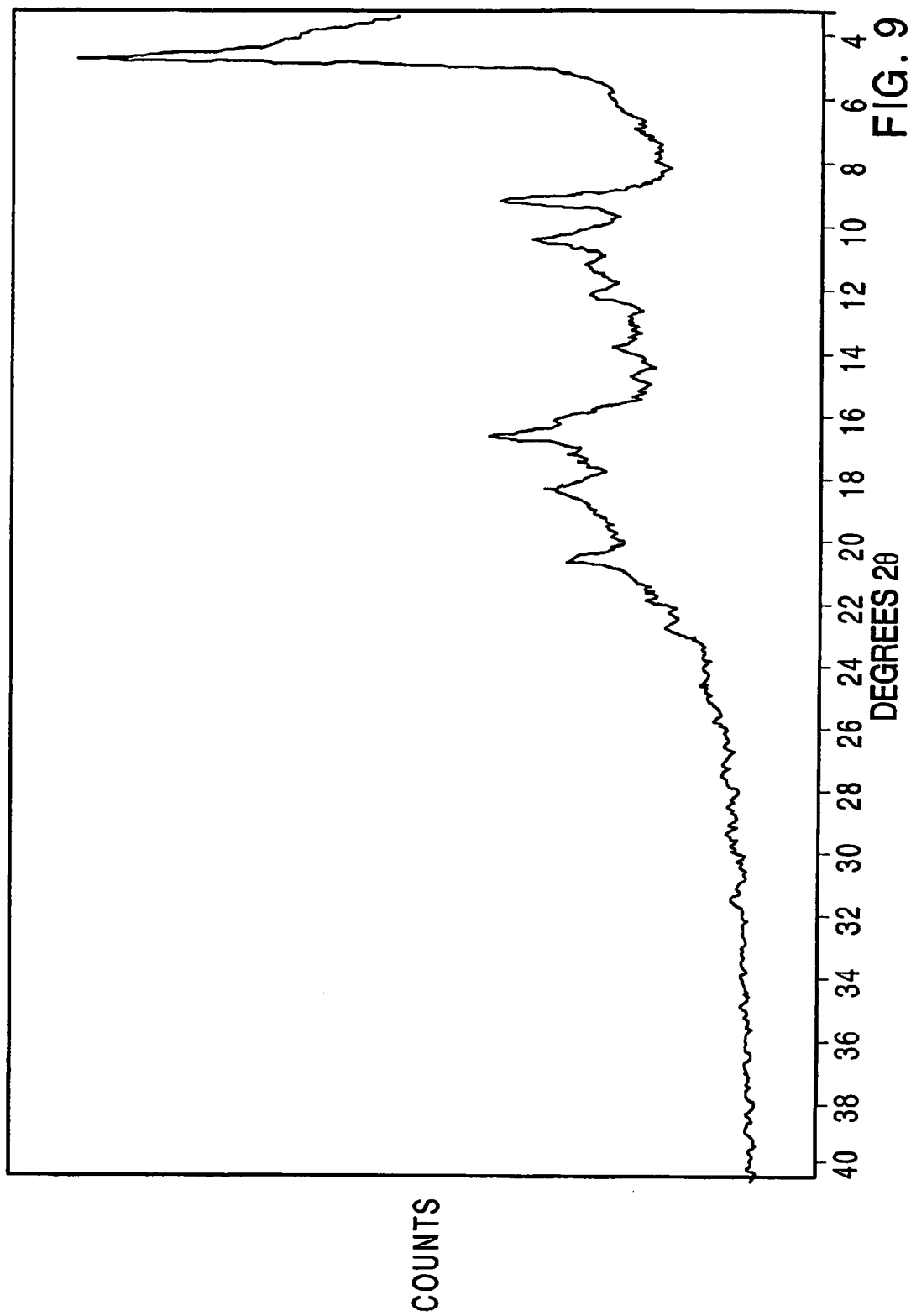
FIG. 9 is a characteristic powder X-ray diffraction pattern of pravastatin sodium Form E.
Figure 10:
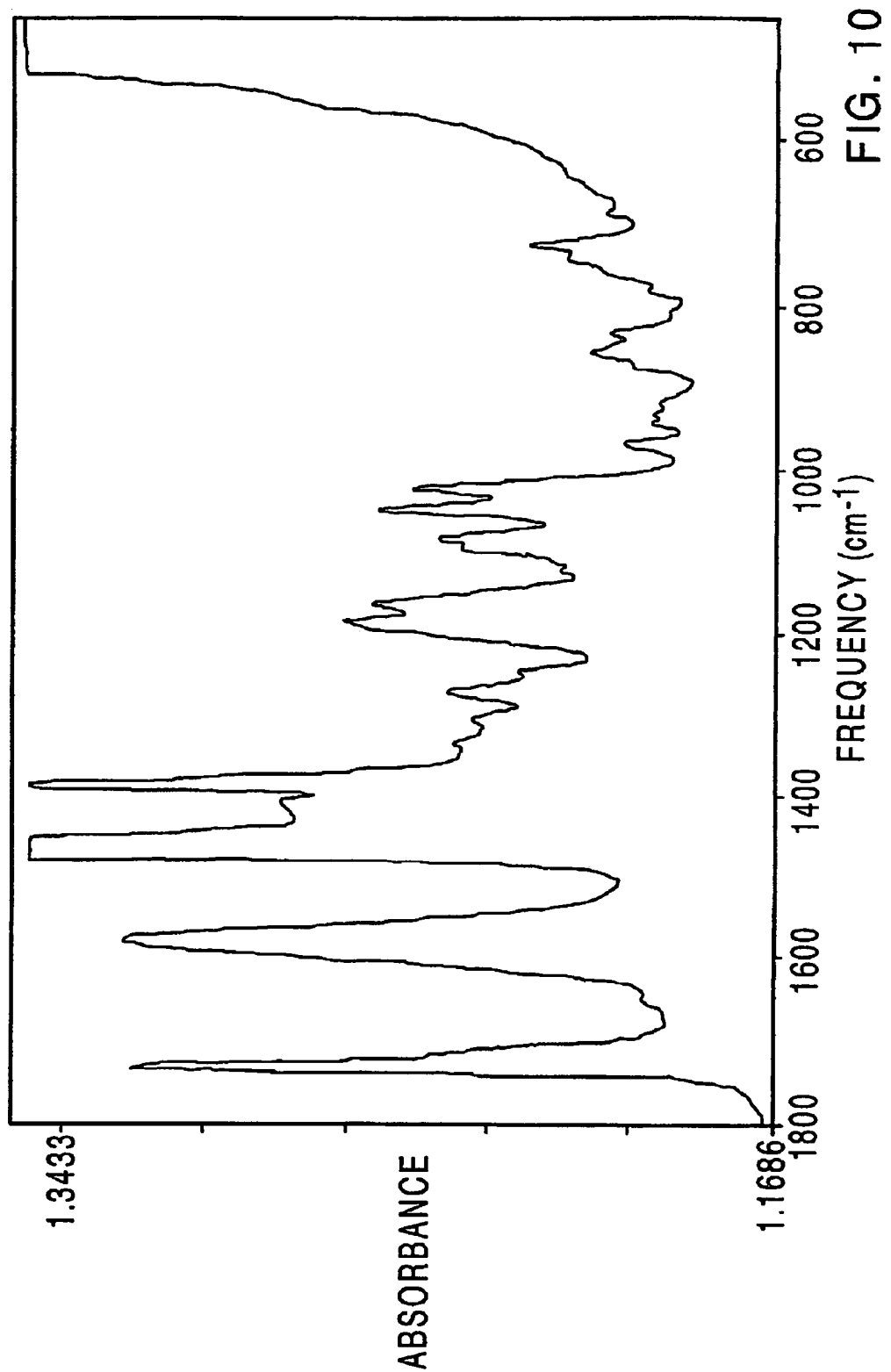
FIG. 10 is a characteristic infrared absorption spectrum of pravastatin sodium Form E.

Pravastatin sodium Form E exhibits reflections in the powder X-ray diffraction pattern at about 4.6, 9.2, 10.3, 11.2, 12.1, 16.6, 18.3 and 20.6±0.2 degrees, detected at a reflection angle of 2θ. Form E is readily distinguished from the other forms of crystalline and amorphous pravastatin sodium by the reflections at 4.6, 9.2, 10.3, 12.1, 16.6, 18.3 and 20.6±0.2 degrees, the reflections at 10.3, 12.1 and 16.6 degrees being especially characteristic of Form E. The diffraction pattern is reproduced in FIG. 9. Form E may further be distinguished by its IR spectrum, provided as FIG. 10, obtained from a Nujol mull. Characteristic absorption bands of pravastatin sodium Form E are observed at 781, 829, 853, 939, 964, 1016, 1043, 1078, 1158, 1179, 1266, 1300, 1329, 1401, 1573 and 1727±2 cm$^{-1}$.

Figure 11:
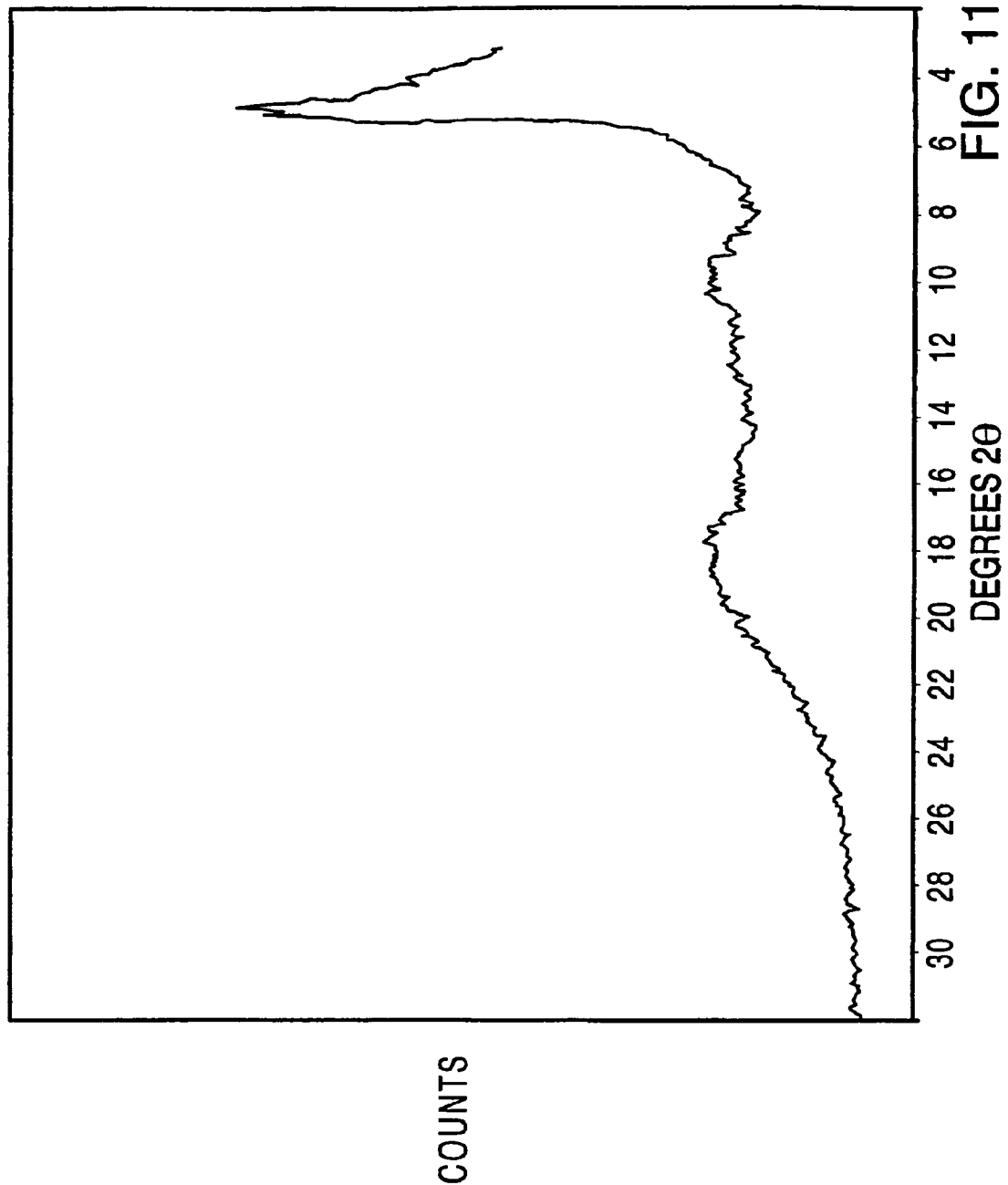
FIG. 11 is a characteristic powder X-ray diffraction pattern of pravastatin sodium Form F.
Figure 12:
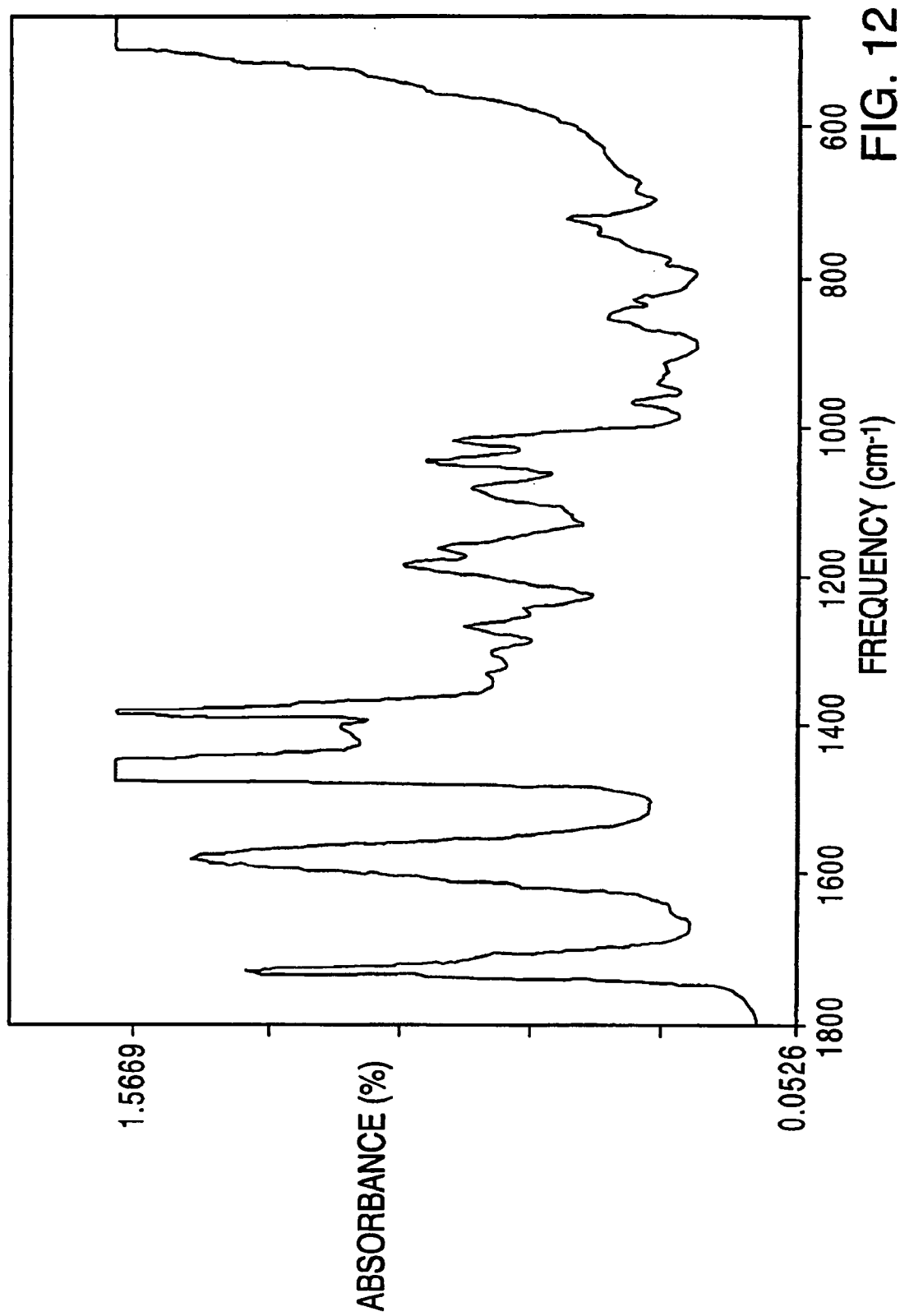
FIG. 12 is a characteristic infrared absorption spectrum of pravastatin sodium Form F.

Pravastatin sodium Form F may be distinguished from the other forms of pravastatin sodium by the reflection in the powder X-ray diffraction pattern that occurs at about 4.6±0.2 degrees, detected at reflection angle 2θ. The absence of other diffraction peaks points to the amorphous nature of this form. The diffraction pattern is reproduced in FIG. 11. Form F may be distinguished by its IR spectrum, provided as FIG. 12, obtained from a KBr window. Absorption bands are observed at 781, 829, 853, 939, 964, 1016, 1043, 1079, 1157, 1181, 1265, 1300, 1330, 1400, 1576 and 1727±2cm$^{-1}$.

Figure 13:
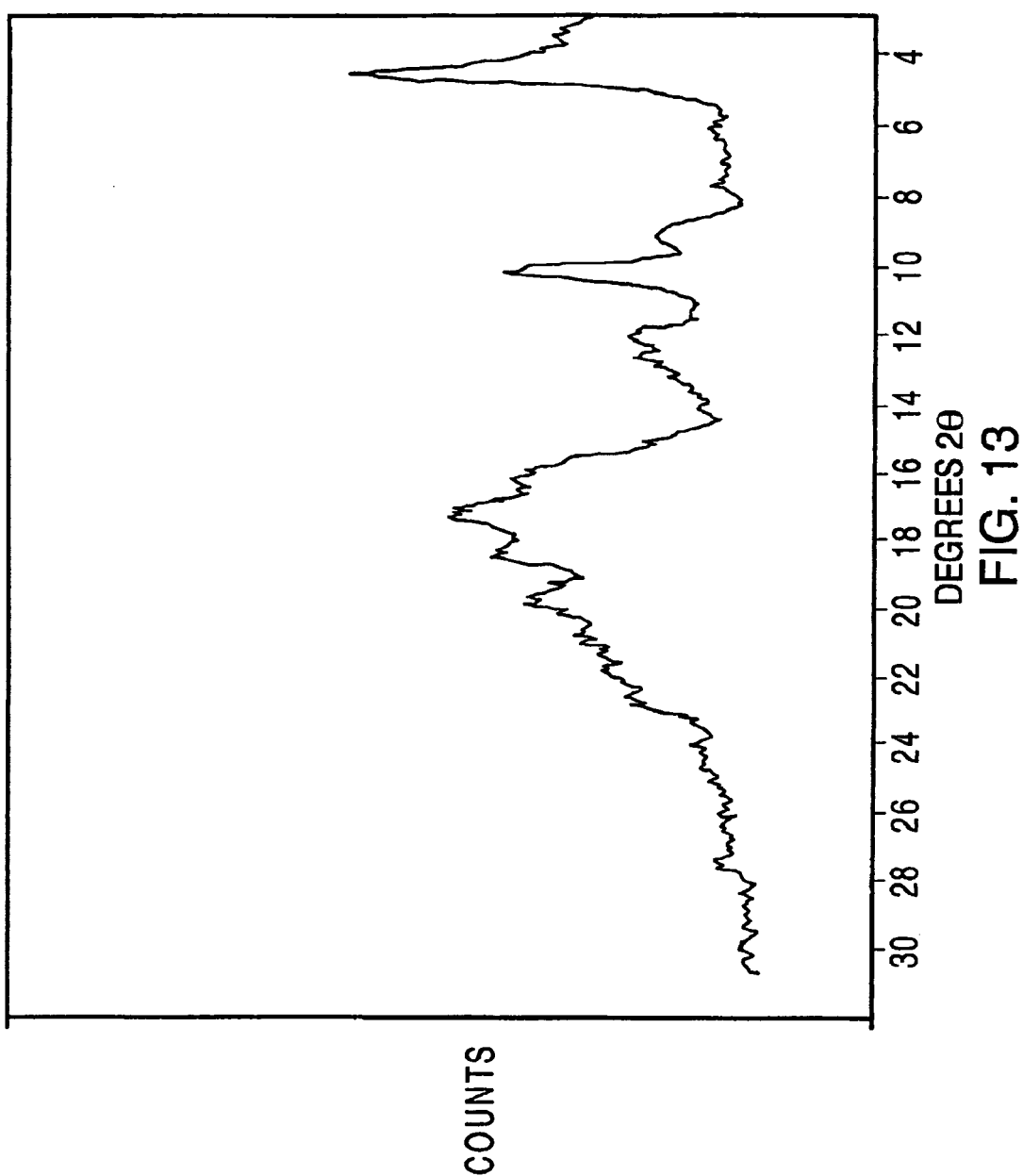
FIG. 13 is a characteristic powder X-ray diffraction pattern of pravastatin sodium Form G.

Pravastatin sodium Form G may be distinguished by reflections in the powder X-ray diffraction pattern that are observed at about 4.5, 9.2, 10.0, 12.2, 16.0, 16.5, 17.6, 18.6, 19.5, 20.5, and 22.8±0.2 degrees, detected at reflection angle 2θ. The diffraction pattern is reproduced in FIG. 13. Pravastatin sodium Form G has a DSC scan characterized by two endotherms at about 165° and 173° C. followed by decomposition.

Figure 14:
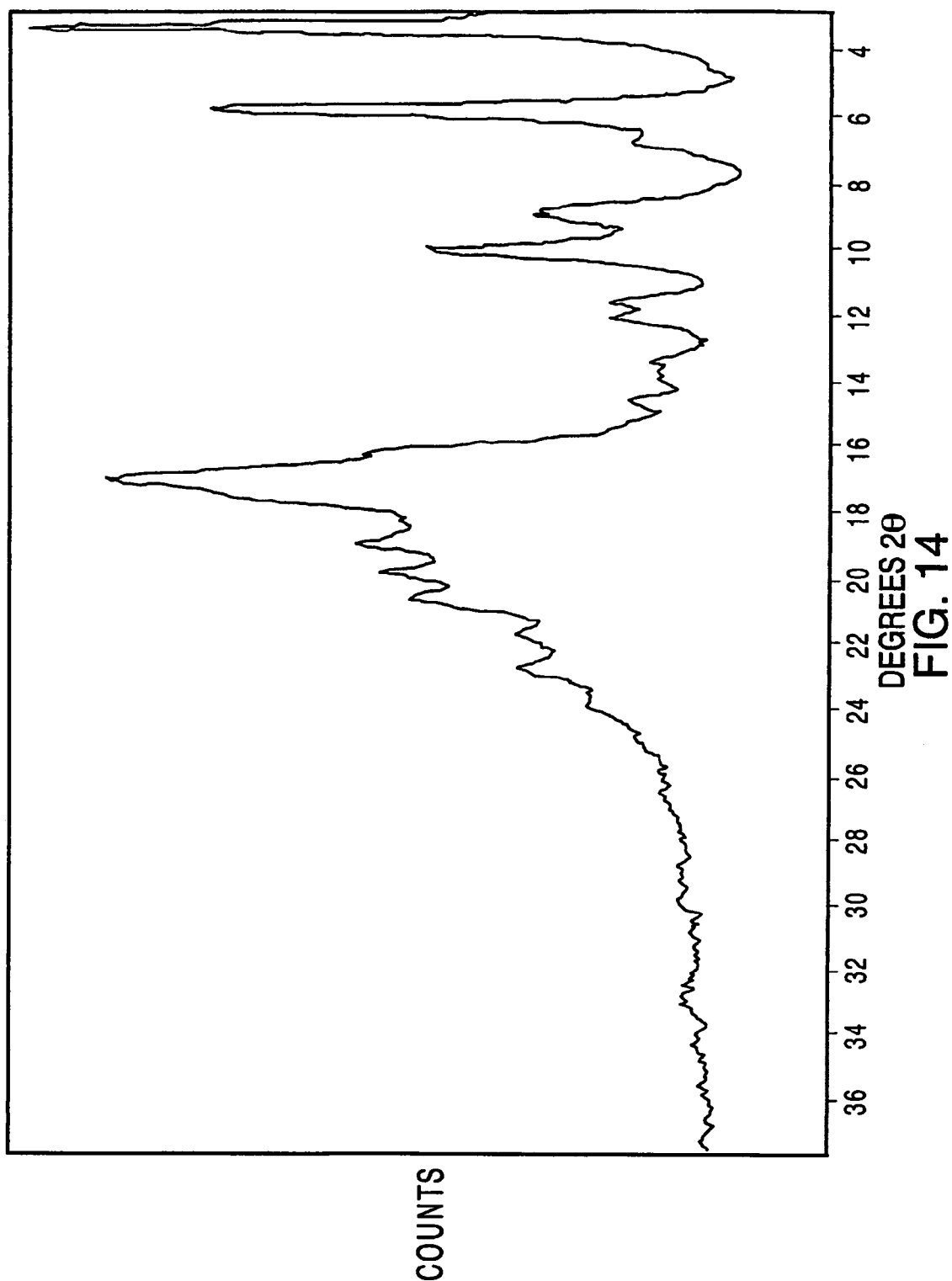
FIG. 14 is a characteristic powder X-ray diffraction pattern of pravastatin sodium Form H.

Pravastatin sodium Form H may be distinguished by reflections in the powder X-ray diffraction pattern that are observed at about 3.5, 5.9, 9.0, 10.1, 11.7, 12.1, 14.7, 17.0 19.0, 19.9, 20.6, 21.8 and 22.9±0.2 degrees, detected at reflection angle 2θ. Of these, the peaks at 3.5, 5.9, 9.0, 10.1 and 17.0±0.2 degrees are particularly diagnostic. The diffraction pattern is reproduced in FIG. 14.

Figure 15:
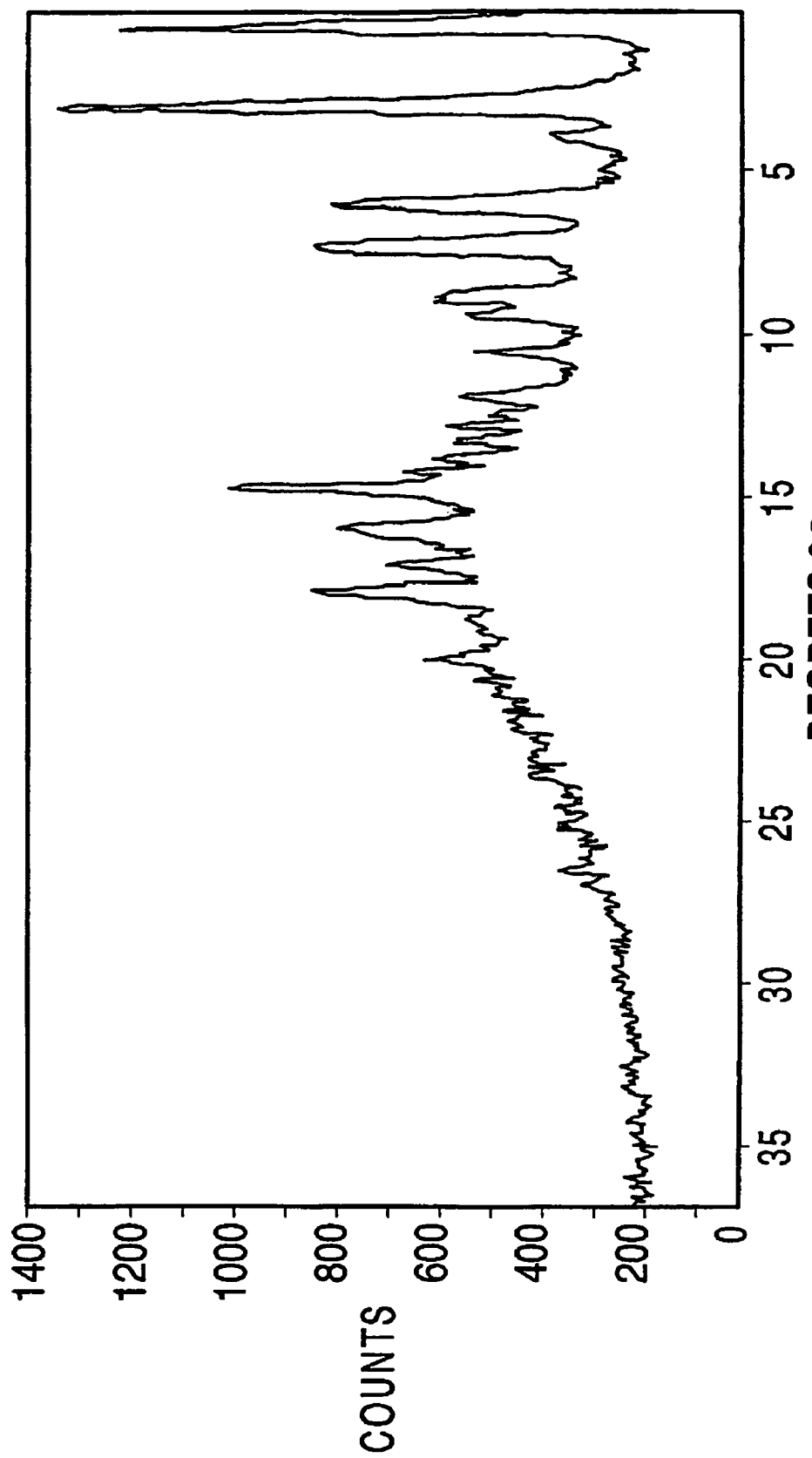
FIG. 15 is a characteristic powder X-ray diffraction pattern of pravastatin sodium Form H1.

Pravastatin sodium Form H1 may be distinguished from the other forms of crystalline and amorphous pravastatin sodium by reflections in the powder X-ray diffraction pattern that are observed at about 3.5, 5.9, 6.8, 8.9, 10.1, 11.7, 12.3, 13.3, 14.8, 17.6, 18.8, 20.0, 20.8, and 22.9±0.2 degrees, detected at reflection angle 2θ. Of these, the peaks at 3.5, 5.9, 8.9, 10.1, 17.6, 18.8 and 20.8±0.2 degrees are particularly diagnostic. The diffraction pattern is reproduced in FIG. 15.

Figure 16:
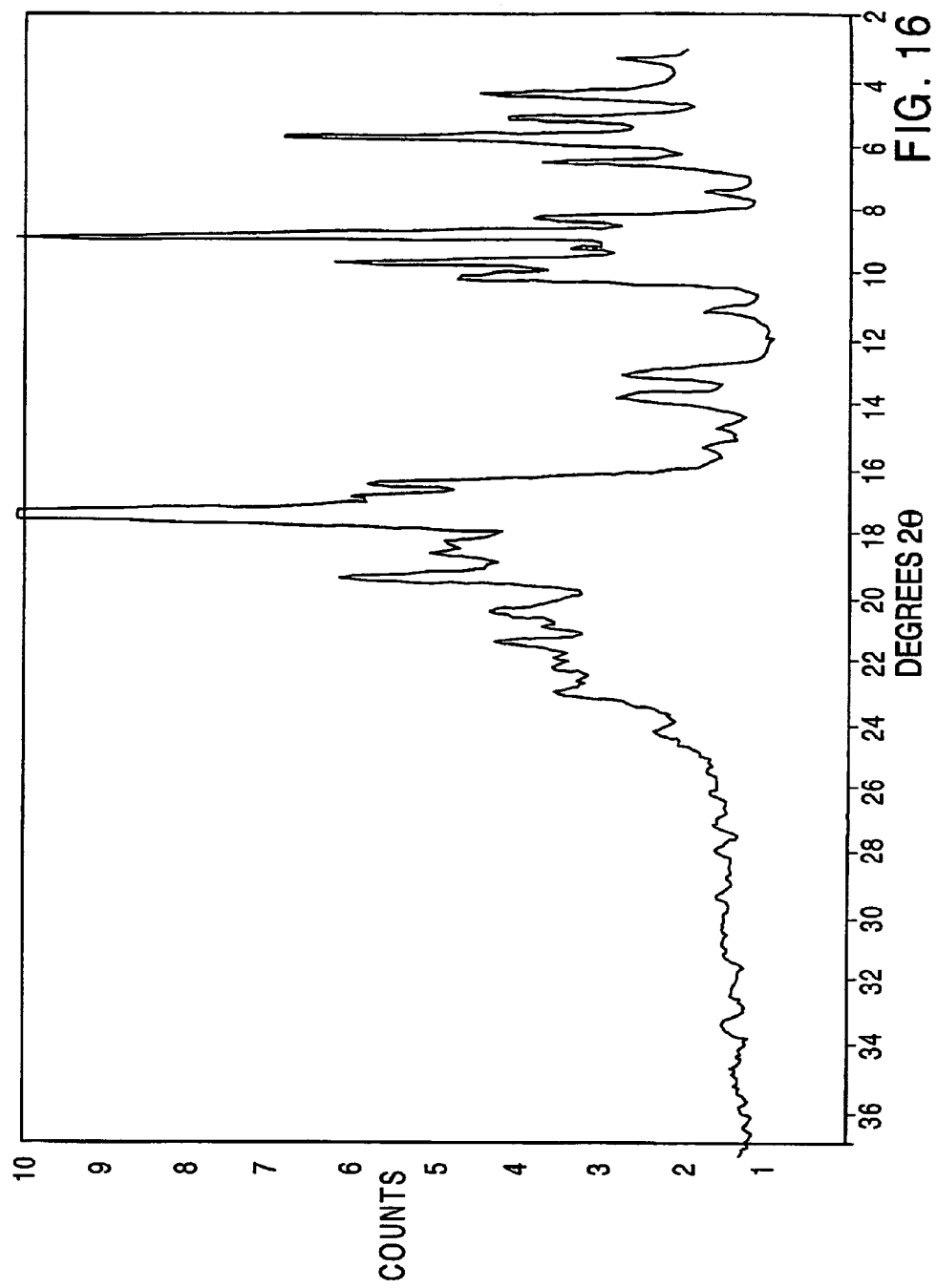
FIG. 16 is a characteristic powder X-ray diffraction pattern of pravastatin sodium Form I.

Pravastatin sodium Form I may be distinguished from the other forms of crystalline and amorphous pravastatin sodium by reflections in the powder X-ray diffraction pattern that are observed at about 4.4, 5.2, 5.8, 6.5, 7.5, 8.3, 9.0, 9.8, 10.2, 11.2, 13.2, 14.0, 16.5, 17.5, 18.3, 18.7, 19.5, 20.5, 21.5 and 23.0±0.2 degrees, detected at reflection angle 2θ. Of these, the peaks at 4.4, 5.2, 5.8, 6.5, 9.0, 13.2, and 14.0±0.2 degrees are particularly diagnostic. The diffraction pattern is reproduced in FIG. 16.

Figure 17:
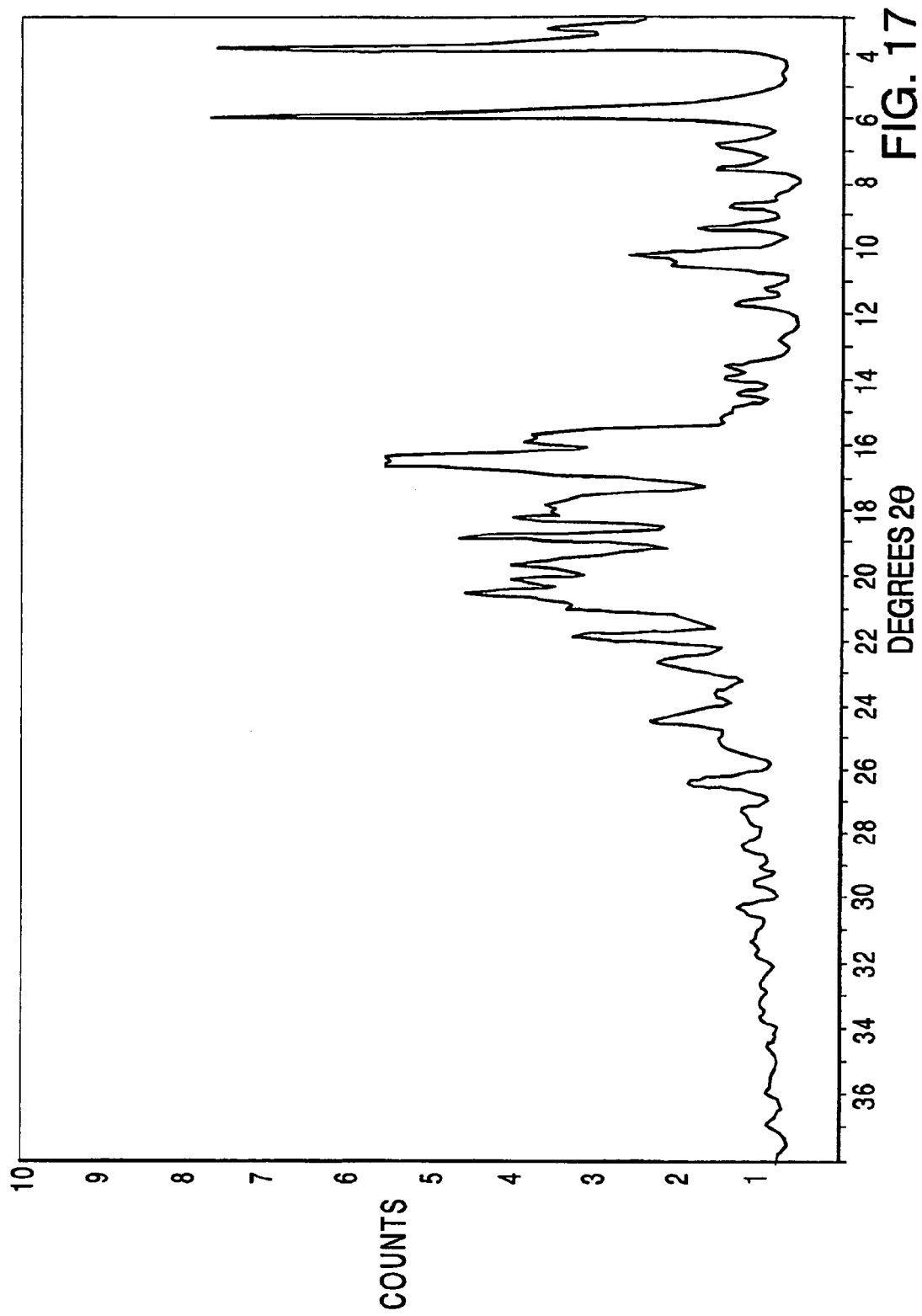
FIG. 17 is a characteristic powder X-ray diffraction pattern of pravastatin sodium Form J.

Pravastatin sodium Form J may be distinguished from the other forms of crystalline and amorphous pravastatin sodium by reflections in the powder X-ray diffraction pattern that are observed at about 3.3, 3.8, 6.0, 6.8, 7.5, 8.8, 9.3, 10.2, 11.2, 11.7, 13.5, 13.9, 14.5, 15.6, 16.3, 17.7, 18.1, 18.7, 19.5, 20.0, 20.4, 21.7, 22.3, 24.2, and 26.1±0.2 degrees, detected at reflection angle 2θ. Of these, the peaks at 3.8, 6.0, and 16.3±0.2 degrees are particularly diagnostic. The diffraction pattern is reproduced in FIG. 17.

Figure 18:
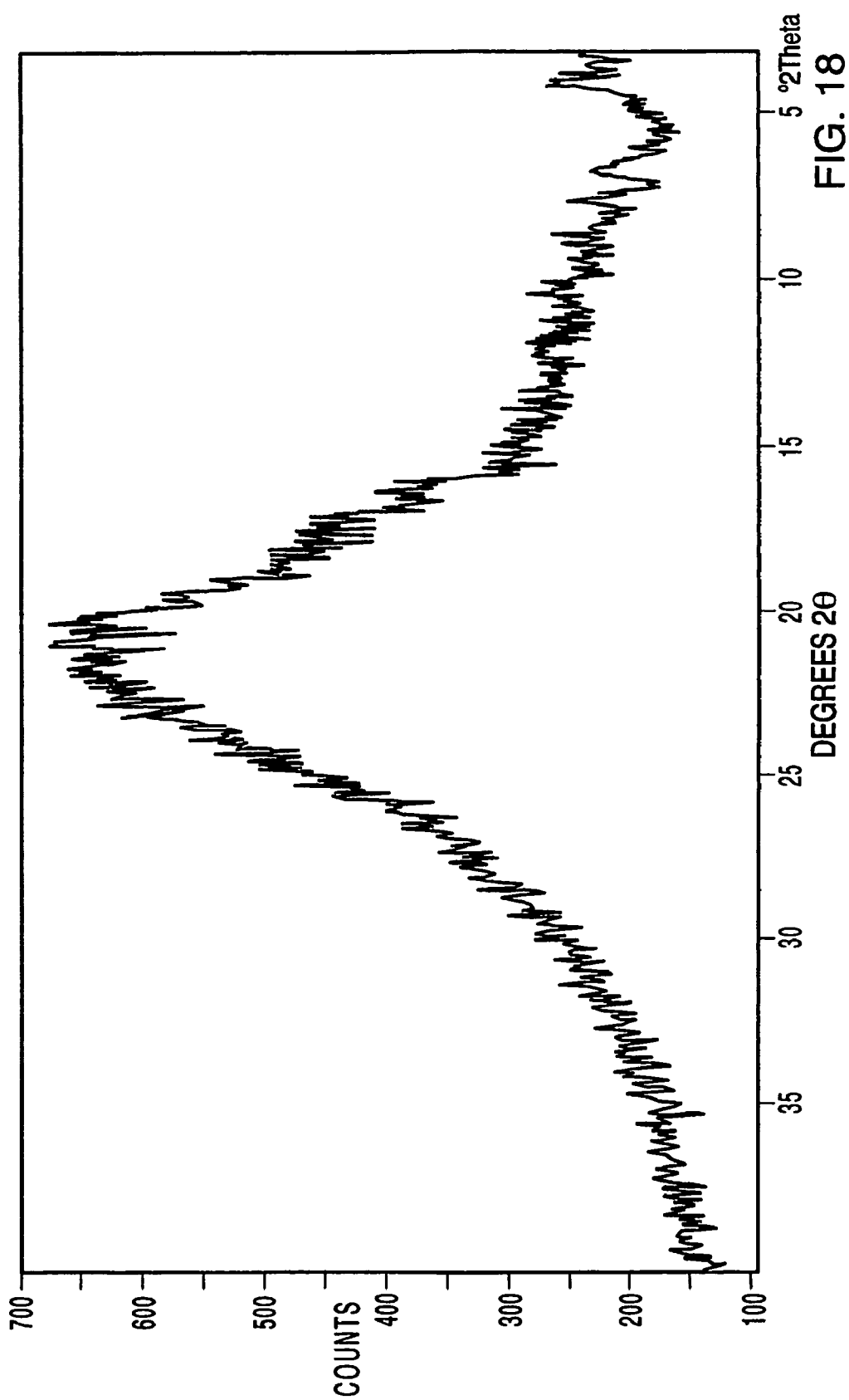
FIG. 18 is a characteristic powder X-ray diffraction pattern of pravastatin sodium Form K.

Pravastatin sodium Form K may be distinguished by reflections in the powder X-ray diffraction pattern that are observed as a broad peak between 15 and 25 as well as peaks at 4.1, 6.8 and 10.2 degrees measured at reflection angle 2θ. The diffraction pattern is reproduced in FIG. 18.

Figure 19:
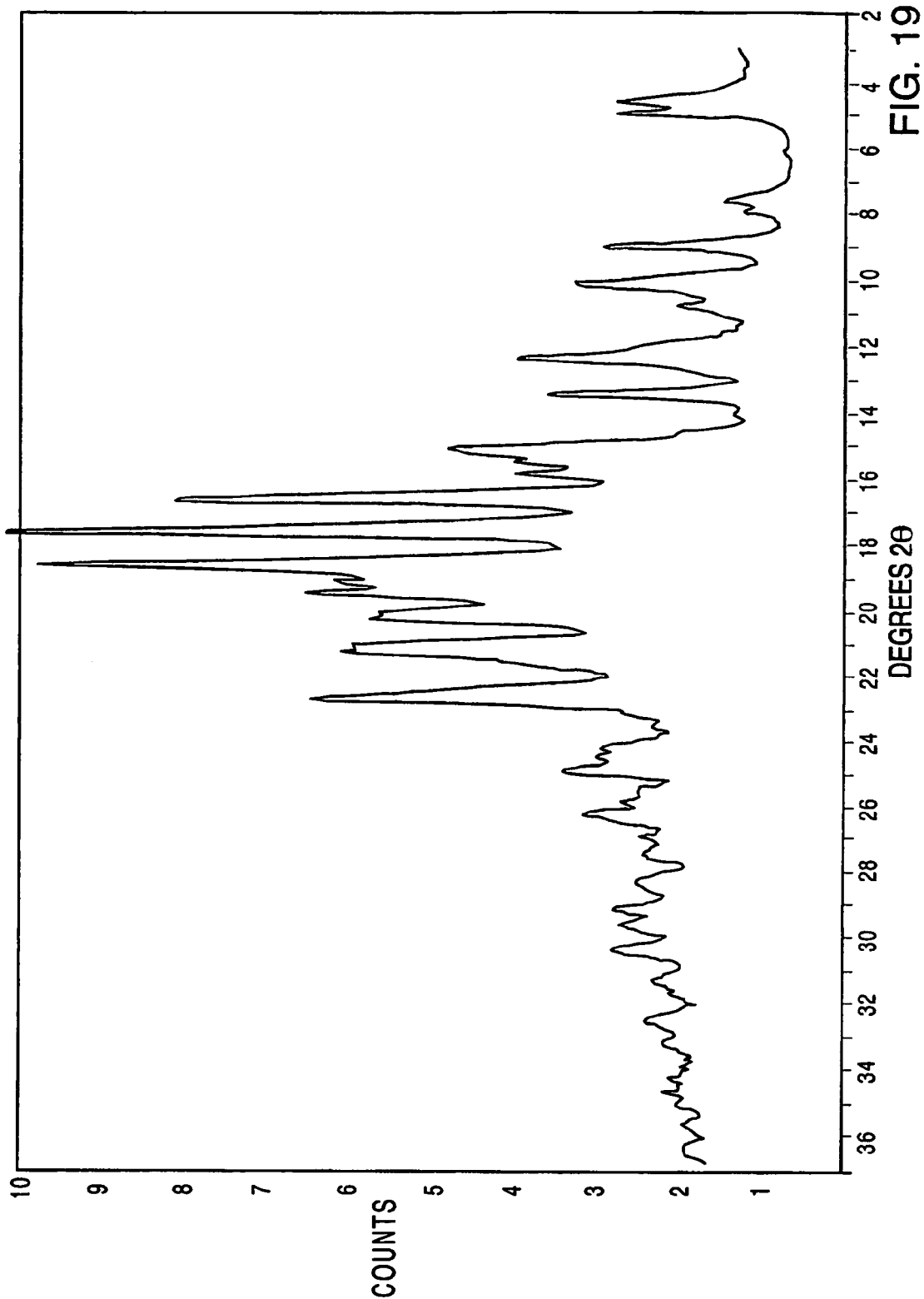
FIG. 19 is a characteristic powder X-ray diffraction pattern of pravastatin sodium Form L.

Pravastatin sodium Form L may be distinguished from the other forms of crystalline and amorphous pravastatin sodium by reflections in the powder X-ray diffraction pattern that are observed at about 4.5, 5.0, 9.0, 10.1, 12.3, 13.4, 15.0, 16.6, 17.6, 18.5 19.5, 20.2, 21.2 and 22.7±0.2 degrees, detected at reflection angle 2θ. Of these, the peaks at 16.6, 17.6, and 18.5±0.2 degrees are particularly diagnostic. The diffraction pattern is reproduced in FIG. 19.

Procedures for Crystallizing Polymorphs of Pravastatin Sodium

It will be appreciated by those skilled in the art of crystallization that attainment of a particular crystalline form of a compound is highly dependent upon exacting control of conditions. These conditions include, among other parameters, the composition of the solvent system employed, the pH of the solvent system, the temperature profile and the form of any crystals that are added to induce crystallization from a supersaturated solution.

Pravastatin sodium Forms A though F may each be obtained by recrystallization from two-component solvent systems having a protic component and an aprotic component. The term "protic" refers to the presence of a labile proton like a hydroxyl proton or carboxylic acid proton. Water is a protic solvent. "Aprotic" means the absence of labile protons. The term "solvents" is used conventionally to mean chemical compounds into which a solute, such as pravastatin sodium, is dissolved or dispersed.

The pravastatin sodium polymorphs A-F, obtained by recrystallization, are highly dependent upon the solvent system from which the form is crystallized. Pravastatin sodium tends to crystallize as Forms A, B and E from solvent systems having a protic component that is either ethanol or an ethanol:water mixture. In contrast, pravastatin sodium tends to crystallize as forms C, D and F from solvent systems that have a protic component that is water alone. We have been able to obtain each of the different forms described above by crystallizing pravastatin sodium from a solvent mixture consisting of a protic solvent and an aprotic solvent. The aprotic solvent is selected from ethyl acetate, acetonitrile, acetone and acetonitrile:acetone mixtures.

Temperature is another important parameter for, among other reasons, its effect on the economics of producing a particular form. It is highly desirable to be able to conduct a crystallization of pravastatin sodium at temperatures of −10° C. or above. −10° C. is approximately the lower limit of temperatures that are obtainable by cooling with cold brine. To obtain lower temperatures, a specialized cooling apparatus, or equivalently, a cooled material like dry ice or liquid nitrogen that has been made cold with a special cooling apparatus must be used. Consequently, the attainment of lower temperatures increases the cost of production. The increased cost may, in fact, be enough to discourage the use of pharmaceuticals in certain crystalline forms with an attendant sacrifice in solubility properties and other desirable properties of the crystalline forms. Accordingly, we have developed procedures for crystallizing pravastatin sodium in each of the forms of the present invention that may be conducted at a crystallization temperature of about −10° C. or above. The choice to use a lower temperature is within the province of one skilled in the art informed by this disclosure.

In order to obtain each of the pravastatin sodium Forms A through F in high yield with only moderate cooling, solvent systems that are moderately to highly concentrated (i.e. typically greater than 0.05 M) in pravastatin sodium have been developed. According to these preferred solvent systems, the pravastatin sodium is preferably first dissolved in the protic component of the solvent system. Then, the protic component is preferably diluted with the aprotic component in order to decrease the solubility of the pravastatin sodium. The concentration of the pravastatin sodium in the protic component before dilution is not critical. However, after dilution, the concentration of pravastatin sodium is preferably in the range of 0.05 to 0.5 M. Dilution may be conducted either before, during or after cooling the solution to the crystallization temperature.

The aprotic solvent may be a nonpolar solvent, such as hexane, petroleum ether, carbon tetrachloride and the like. The aprotic solvent may also be a polar aprotic solvent. In particular, acetonitrile, acetone, ethyl acetate and acetonitrile:acetone mixtures comprise a spectrum of aprotic components from which each of the novel pravastatin sodium forms may be obtained. Aprotic solvents are preferably used from 4 to 20 fold excess on a volume-to-volume basis over the protic component.

The use of ethanol alone as the protic component of the solvent system favors the crystallization of pravastatin sodium Form B, provided the solvent system has been adjusted to a pH of about 8.2 to about 8.7, preferably about 8.5. Equal-volume mixtures of ethanol and water, on the other hand, tend to favor crystallization of Form A. Comparison of Examples 1 and 2 with Example 3 demonstrates this solvent effect with specific illustrative embodiments.

While, generally speaking, the form of pravastatin sodium obtained by recrystallization is not especially sensitive to the choice of aprotic solvent among these exemplary aprotic solvents, it will be noted that the use of ethyl acetate in a 20:1 excess over a 1:4 H$_2$O:ethanol protic component promotes crystallization of pravastatin sodium in Form E (See Example 8). This result is to be compared to crystallization from ethanol and ethanol:water mixtures in Forms A and B which is promoted by an acetonitrile aprotic component (See Examples 1-3). In addition, when the acetonitrile is used in an amount that is around the lower range of the proportion of aprotic component in the solvent system, i.e. about 4 to about 7 fold excess over the protic component, pravastatin sodium Form B is favored. On the other hand, when acetonitrile is used in an intermediate amount, i.e. about 13 to about 17 fold excess, Form A is favored.

As noted above, a solvent system having a protic component of water alone favors the section crystallization of pravastatin sodium as Forms C, D or amorphous Form F. Formation of amorphous Form F is promoted by adjustment of the pH of the solvent system from about pH 8.7 to about pH 10.3, preferably about pH 9 to about pH 10. The pH may be adjusted by contacting with a weak cationic exchange resin such as Amberlite® IRC-50 (See Examples 9 and 10). If the pH is not adjusted, Form F typically is not obtained in pure form. Forms C and D may be obtained from a solvent system wherein water is the only protic component and wherein the pH of the solution is not adjusted for the purpose of obtaining Form F.

None of the aforementioned parameters operates independently. So, in the examples concluding this description and preceding the claims, which disclose the best mode for obtaining each of the forms, it will be seen that variations in several parameters at once combine to produce an optimal yield and purity of the desired form. In particular, the choice of solvent system, concentration and temperature profile are not independent. The use of acetonitrile, acetone and acetonitrile:acetone mixtures as the aprotic component, rather than ethyl acetate, allows for a greater concentration of pravastatin sodium in solution at ambient temperature without premature crystallization. Thus, without heating of the solution of pravastatin sodium in the protic component prior to dilution, the solution may be diluted with acetone and/or acetonitrile to a range of 0.1 to 0.2 M without premature crystallization (See, e.g. Examples 7, 9-11). When ethyl acetate is used as the aprotic component, the solution of pravastatin sodium in the protic component is preferably heated to about 40° C. or above, more preferably about 60° C. before addition of the ethyl acetate. Preferably, with heating, ethyl acetate is added to dilute the solution to less than 0.1 M.

The rate of cooling from ambient or elevated temperature, whichever the case may be, should not be excessively rapid in order to realize maximum selectivity of the other conditions that have been chosen in order to obtain the desired form. Rapid cooling, typically, will tend to reduce selectivity and result in mixtures of two or more forms rather than an individual pure form. Accordingly, manipulation of the recrystallization parameters to obtain mixtures of the novel forms of pravastatin having desirable characteristics is considered to be within the scope of the invention. Typically, in order to obtain any one of the forms in high purity the rate of cooling may be about from 2° C. h$^{-1}$ to 35° C. h$^{-1}$, but the rate of cooling is preferably between about 2° C. h$^{-1}$ to 5.8° C. h$^{-1}$.

Once crystallization is complete, the crystals are then isolated by filtration, decantation of the solvent, removal of the solvent or other such method, preferably filtration. The crystals optionally may then be washed and dried according to methods known to the art.

Pravastatin sodium Form G may be prepared by storing pravastatin sodium Form F for 2 weeks at a relative humidity of about 40 to about 80%.

Pravastatin sodium Forms A, H, H1, I, J, K may each be obtained by conversion from Form D or F. The conversion process consists of treating pravastatin sodium Form D or F with an alcohol. In one embodiment the alcohol treatment consists of exposing the first polymorph to the vapors of a solvent for a time period. The period of time may be overnight or may last for three weeks. In an alternative embodiment the solvent treatment comprises suspended Form D or F in a solvent for a period of time.

The treatment is performed at room temperature. The temperature may be between about 15° C. and 35° C. Optimally, the temperature is about 25° C.

The polymorphic form of pravastatin sodium obtained is dependent on the treatment solvent. For example, treating Form D or F with ethanol vapors produces Form A. Treating form D or F with methanol vapors produces Form H. The relationship between the treatment solvent and the polymorphic form of pravastatin sodium produced is summarized in Table I, and illustrated in Example 15, 16, 17, 18, 19, and 20.

TABLE I

| Starting Polymorph | Resulting Polymorph | Solvent | Incubation Time | Exposure |
|---|---|---|---|---|
| D or F | A | Ethanol | 3 weeks | Vapors |
| D or F | H | Methanol | 3 weeks | Vapors |
| D or F | H1 | Methanol | Overnight | Suspension |
| D or F | I | Isopropyl Alcohol | 3 weeks | Vapors |
| D or F | J | Butanol | 3 weeks | Vapors |
| D or F | K | Ethanol, Isopropyl Alcohol and Butanol | Overnight | Suspension |

Most of these forms have a jelly appearance. By drying these samples at 60° C., vacuum overnight, the powdered Form D is obtained.

Treatment of Hypercholesteremia with Pravastatin Sodium Polymorphs

More pravastatin sodium Forms A, B, C, D, E, F, G, H, H1, I, J, K and L are useful for hypercholesteremia therapy and for this purpose they are administered to a mammalian patient in a dosage form. Dosage forms may be adapted for administration to the patient by oral, buccal, parenteral, ophthalmic, rectal and transdermal routes. Oral dosage forms include tablets, pills, capsules, troches, sachets, suspensions, powders, lozenges, elixirs and the like. The pravastatin sodium forms also may be administered as suppositories, ophthalmic ointments and suspensions, and parenteral suspensions, which are administered by other routes. The most preferred route of administration of the pravastatin sodium forms of the present invention is oral.

While the description is not intended to be limiting, the invention does not pertain to true solutions of any of the novel pravastatin sodium forms in which the properties of the solid forms of pravastatin sodium are lost. However, the use of the novel forms to prepare such solutions (e.g. so as to deliver, in addition to pravastatin sodium, a solvate to said solution in a certain ratio with a solvate) is considered to be within the contemplated invention.

The dosage forms may contain one or more of the novel forms of pravastatin sodium or, alternatively, may contain one or more of the novel forms of pravastatin sodium in a composition. Whether administered in pure form or in a composition, the pravastatin sodium form(s) may be in the form of a powder, granules, aggregates or any other solid form. The compositions of the present invention include compositions for tableting. Tableting compositions may have few or many components depending upon the tableting method used, the release rate desired and other factors. For example, compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin.

Further excipients that are within the contemplation of the present invention include binders, such as acacia gum, pregelatinized starch, sodium alginate, glucose and other binders used in wet and dry granulation and direct compression tableting processes. Excipients that may also be present in a solid composition of the novel forms of pravastatin sodium further include disintegrants like sodium starch glycolate, crospovidone, low-substituted hydroxypropyl cellulose and others. Additional excipients include tableting lubricants like magnesium and calcium stearate and sodium stearyl fumarate; flavorings; sweeteners; preservatives; pharmaceutically acceptable dyes and glidants such as silicon dioxide.

Capsule dosages, of course, will contain the solid composition within a capsule which may be made of gelatin or other encapsulating material. Tablets and powders may be coated. Tablets and powders may be coated with an enteric coating. The enteric-coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

In human subjects with normal hepatic function and moderate body weight, a reduction in serum cholesterol levels is typically observed with daily dosages of 10 mg or more of pravastatin sodium. A daily oral regimen is the most commonly prescribed method of administration. Preferred oral dosages of the present invention contain from about 10 mg to about 40 mg of pravastatin sodium Forms A, B, C, D, E, F, G, H, H1, I, J, K, and L or their mixtures.

Having thus described the present invention with reference to certain preferred embodiments, the following examples are provided to further illustrate methods by which novel Forms A, B, C, D, E, F, G, H, H1, I, J, K, and L of pravastatin sodium may be obtained. One skilled in the art will recognize variations and substitutions in the methods as described and exemplified which do not depart from the spirit and scope of the invention.

EXAMPLES

"Ethanol" refers to absolute ethanol. Acetonitrile, acetone and ethyl acetate were regular grade.

Example 1

Preparation of Pravastatin Sodium Form A

Pravastatin sodium (5 g) was dissolved in a 1:1 mixture of ethanol:water (5 ml). The pH was raised to 8.5 by addition of 2M sodium hydroxide in water (1.2 ml) and the solution was heated to 50° C. Acetonitrile (90 ml) was added to the mixture and then the mixture was stirred at elevated temperature for one hour. The mixture was allowed to cool to 20-25° C. ("ambient temperature"), was held at ambient temperature for two hours and then cooled to 5° C. and maintained at 5° C. for 12 hours, whereupon pravastatin sodium crystallized. The crystals were then isolated by filtration and washed with acetonitrile (2×10 ml) and dried under vacuum at 50° C. X-ray diffraction analysis revealed the presence of Form A. Pravastatin Form A was obtained in 92% yield.

Example 2

Preparation of Pravastatin Statin Form A

Pravastatin sodium (5 g.) was dissolved in a 2.85:1 mixture of ethanol:water (10.8 ml). The pH was raised to 8.5 by addition of 2M sodium hydroxide in water (1.2 ml). Acetonitrile (200 ml) was then slowly added to the mixture at ambient temperature over a two hour period. The mixture was stirred at ambient temperature for another two hours and then cooled to 5° C. and maintained at 5° C. for 12 hours, whereupon pravastatin sodium crystallized. The crystals were then isolated by filtration and washed with acetonitrile (2×10 ml) and dried under vacuum at 50° C. X-ray diffraction analysis revealed the presence of Form A. Pravastatin sodium Form A was obtained in 96% yield.

Example 3

Preparation of Pravastatin Sodium Form B

Pravastatin sodium (5 g) was dissolved in ethanol (35.5 ml). The pH was raised to 8.5 by addition of 2M sodium hydroxide in water (1.5 ml). The basic solution was heated to 60° C. and then diluted with acetonitrile (213 ml). The solution was maintained at elevated temperature for one hour and then was allowed to cool to ambient temperature and was maintained at ambient temperature for two hours. The solution was then cooled to 5° C. and maintained at that temperature for 12 hours, whereupon pravastatin sodium crystallized. The crystals were isolated by filtration and rinsed, first with ethyl acetate (2×45 ml) and second with n-hexane (2×45 ml). The rinse solvents had been precooled to 5° C. After rinsing, the crystals were dried under vacuum at 50° C. X-ray diffraction analysis revealed the presence of Form B. Pravastatin sodium Form B was obtained in 87% yield.

Example 4

Preparation of Pravastatin Sodium Form C

Pravastatin sodium (10 g) was dissolved in deionized water (26 ml) and diluted with a 2:3 mixture of acetonitrile:acetone (130 ml). The resulting solution was then warmed to 40° C. and maintained at that temperature for one half hour while acetonitrile (160 ml) was slowly added. The solution was then cooled to 5° C. While cooling, pravastatin sodium began to crystallize at 19.5° C. The mixture was maintained at 5° C. for five hours, after which time the crystals were isolated by filtration, washed with acetone that had been pre-cooled to 5° C., and dried under vacuum at 50° C. X-ray diffraction analysis revealed the presence of Form C. Pravastatin sodium Form C was obtained in 76% yield.

Example 5

Preparation of Pravatatin Sodium Form D

Pravastatin sodium (600 g) was dissolved in 0.73 M sodium hydroxide in water (600 ml). The resulting solution was diluted with acetonitrile (1.2 L) and then decolorized by stirring over charcoal (30 g) for 30 min. The charcoal was removed by filtration and rinsed with 2:1 acetone:water (1.8 L). The pravastatin sodium solution and rinsate were combined and diluted with acetonitrile (17 L). The dilute solution was maintained at ambient temperature (20-25° C.) for one hour and then cooled to 5° C. and stirred at that temperature for 4 hours, whereupon pravastatin sodium crystallized. The crystals were filtered and slurried with ethyl acetate (6 L) at 5° C. to remove residual acetonitrile. The crystals were then washed with ethyl acetate that had been pre-cooled to −5° C. and dried under vacuum at 50° C. X-ray diffraction analysis revealed the presence of Form D. Pravastatin sodium Form D was obtained in 97% yield.

Example 6

Preparation of Pravastatin Sodium Form D

Pravastatin sodium (7 g) was dissolved in deionized water (13 ml) and diluted with acetone (14.3 ml). The resulting solution was stirred over charcoal (0.07 g.) to decolorize. The charcoal was removed by filtration and rinsed with a 10:1 mixture of acetone:water (15.7 ml). The combined pravastatin sodium solution and rinsate was then diluted with acetone (42.8 ml) and cooled to −10° C. At the reduced temperature, more acetone (143 ml) was slowly added over one half hour. The solution was then maintained at −10° C. for three hours during which time pravastatin sodium crystallized. The crystals were then isolated by filtration, washed with 1% water in acetone that had been pre-cooled to −10° C. (28 ml) and then again with anhydrous acetone (28 ml). The crystals were then dried under vacuum at 50° C. X-ray diffraction analysis revealed the presence of Form D. The conversion of amorphous pravastatin sodium to pravastatin sodium Form D occurred in 85% yield. Before drying the crystals were Form L, after drying the crystals were Form D.

Example 7

Preparation of Pravastatin Sodium Form D

Pravastatin sodium (25 g) was dissolved in deionized water (65 ml) and diluted with 1:1.44 acetonitrile:acetone (330 ml). The resulting solution was cooled to 5° C. While cooling, pravastatin sodium started to crystallize at 9° C. After crystallization appeared to cease, acetone that had been precooled to 5° C. (650 ml) was added to the mixture and the mixture was maintained at 5° C. for another three hours. The crystals were isolated by filtration and washed with 1:3:22 water:acetone:acetonitrile that had been pre-cooled to 5° C. (25 ml). The crystals were then slurried with ethyl acetate that had been pre-cooled to 5° C. (50 ml) and dried under vacuum at 50° C. X-ray diffraction analysis revealed the presence of Form D. Pravastatin sodium Form D was obtained in 70% yield.

Example 8

Preparation of Pravastatin Sodium Form E

Pravastatin sodium (5 g) was dissolved in 4:1 ethanol:water (12.5 ml) and warmed to 60° C. The solution was then diluted with ethyl acetate (250 ml) and the dilute solution was maintained at elevated temperature for one hour. The solution was then allowed to cool to ambient temperature and was maintained at that temperature for two hours. The solution was then cooled to 5° C. and maintained at reduced temperature for three hours, whereupon pravastatin sodium crystallized. The crystals were isolated by filtration, rinsed with ethyl acetate (2×30 ml) and dried under vacuum at 50° C. X-ray diffraction analysis showed the presence of Form E. Pravastatin sodium Form E was obtained 87% yield.

Example 9

Preparation of Pravastatin Sodium Form F

Pravastatin sodium (10 g) was dissolved in water (24.5 ml) and diluted with acetonitrile (26 ml). The resulting solution was stirred over charcoal (0.1 g.) to decolorize. Amberlite® IRC-50 cationic ion exchange resin ($H^+$ form) was added to the stirred mixture to raise the pH to 9.09. The charcoal and ion exchange resin were removed by filtration and rinsed with a 10:1 mixture of acetonitrile:water (16.5 ml). The combined pravastatin sodium solution and rinsate was diluted with 2.1:1 acetone:acetonitrile (115 ml), cooled to 5° C. and maintained at reduced temperature for two hours. pravastatin sodium crystallized. After crystallization appeared to cease, acetonitrile (260 ml) that had been pre-cooled to 5° C. was added and the mixture was maintained at reduced temperature for another three hours. The crystals were isolated by filtration and washed with 1:3:22 water:acetone:acetonitrile (40 ml) that had been pre-cooled to 5° C. The crystals were then slurried with precooled ethyl acetate (100 ml) and dried under vacuum at 50° C. X-ray diffraction analysis showed the presence of Form F. Pravastatin sodium Form F was obtained in 74% yield.

Example 10

Preparation of Pravastatin Sodium Form F

Pravastatin sodium (10 g) was dissolved in deionized water (24.5 ml) and diluted with acetonitrile (26 ml). The resulting solution was stirred over charcoal (0.1 g.) to decolorize. Then, the pH was raised to 9.01 by addition of Amberlite® IRC-50 cationic exchange resin ($H^+$ form). The charcoal was removed by filtration and rinsed with a 10:1 mixture of acetonitrile:water (16.5 ml). The combined pravastatin sodium solution and rinsate was then diluted with 2.1:1 acetone:acetonitrile (115 ml) and cooled to 5° C. The solution was maintained at reduced temperature for three hours, during which time pravastatin sodium crystallized. The crystals were isolated by filtration and washed with 1:3:22 water:acetone:acetonitrile that had been pre-cooled to 5° C. (40 ml). The crystals were slurried with ethyl acetate that had been pre-cooled to 5° C. and then dried under vacuum at 50° C. X-ray diffraction analysis showed the presence of Form F. Pravastatin sodium Form F was obtained in 90% yield.

Example 11

Preparation of Pravastatin Sodium Form F

Pravastatin sodium (5 g) was dissolved in deionized water (13 ml) and diluted with acetone (65 ml). The resulting solution was cooled to 5° C. While cooling, pravastatin sodium Form F began to crystallize at 9° C. The mixture was maintained at 5° C. for five hours. Then, acetone that had been pre-cooled to 5° C. was added to the mixture and the mixture was kept at 5° C. for another three hours, after which time crystallization was judged to be complete. The crystals were then isolated by filtration, washed with acetone that had been pre-cooled to 5° C. (10 ml) and dried under vacuum at 50° C. Pravastatin sodium Form F was obtained in 87% yield.

Example 12

Preparation of Mixture of Pravastatin Sodium Forms D and F

Pravastatin sodium (10 g.) was dissolved in deionized water (24.5 ml) and diluted with acetonitrile (26 ml). The resulting solution was stirred over charcoal (0.1 g.) to decolorize. The charcoal was removed by filtration and rinsed with a 10:1 mixture of acetonitrile:water (16.5 ml). The combined pravastatin sodium solution and rinsate was diluted with acetonitrile (11 ml) and warmed to 40° C. At the elevated temperature, acetone (60 ml) was slowly added over one half hour. The solution was then cooled to a temperature of 10° C. over three hours. After the solution had attained a temperature of 12° C., the mixture was seeded with a crystal of pravastatin sodium Form D. At 11.3° C., the solution was diluted with acetone (200 ml). After the three hours had passed, the mixture of solution and crystals was cooled to 5° C. and maintained at that temperature for three hours. The crystals were then removed by filtration, washed with acetone that had been pre-cooled to 5° C. (40 ml) and dried under vacuum at 50° C. The crystals were found by X-ray diffraction to be a mixture of pravastatin sodium Form D and Form F. The mixture of pravastatin sodium Forms D and F was obtained in 77% yield.

Example 13

Preparation of Mixture of Pravastatin Sodium Forms C and D

Pravastatin sodium (10 g) was dissolved in deionized water (18 ml) and diluted with acetone (20 ml). The resulting solution was stirred over charcoal (0.1 g) to decolorize. The charcoal was removed by filtration and rinsed with a 10:1 mixture of acetonitrile:water (20 ml). The combined pravastatin sodium solution and rinsate was then diluted with acetone (60 ml) and warmed to 40° C. The solution was maintained at elevated temperature for half an hour while acetone (190 ml) was slowly added. The solution was cooled to 10° C. While being cooled, the solution was seeded with a crystal of pravastatin sodium Form D at 13° C. The solution was then maintained at 10° C. for three hours. Then acetone (190 ml) was added and the solution was cooled to 5° C. Another 190 ml of acetone was added and the mixture was stirred at 5° C. for three hours, during which time crystallization was complete. The crystals were isolated by filtration, washed with acetone that had been pre-cooled to 5° C., and dried under vacuum at 50° C. The crystals were identified by X-ray diffraction as a mixture of pravastatin sodium Forms C and D. The mixture of pravastatin sodium Forms C and D was obtained in 89% yield.

Example 14

Preparation of Pravastatin Sodium Form F

Pravastatin sodium (10 g) was dissolved in deionized water (20 ml). The pH of the aqueous solution was adjusted to 7.1 by addition of Amberlite® IRC-50 cationic ion exchange resin ($H^+$ form). The solution was then diluted with acetone (120 ml) and then heated to 40° C. Another 130 ml of acetone was slowly added to the mixture over a period of 30 min. The solution was then cooled to 5° C. over 3 hours. When the mixture reached a temperature of 25° C., it was seeded with crystals of Form F. The mixture was maintained at 5° C. for 20 h, over which time pravastatin sodium crystallized from the mixture. The crystals were isolated by filtration and washed with acetone (40 ml). The crystals were then dried under vacuum at 60° C. X-ray diffraction analysis showed the presence of Form F. Pravastatin sodium Form F was obtained in 84% yield.

Example 15

Preparation of Pravastatin Sodium Form G

Pravastatin Form G is obtained when pravastatin Form F is stored for two weeks at relative humidity of between 40-80%. The resulting solid was analyzed by X-ray diffraction without further treatment.

Example 16

Preparation of Pravastatin Sodium Form H

Pravastatin sodium Form H was prepared by treating Form D or F with ethanol vapors for three weeks at room temperature. The procedure was as follows. A 100-200 g sample of pravastatin sodium Form D or F was kept in a 10 ml open glass bottle. The open bottle was introduced into a larger bottle containing ethanol. The larger bottle was sealed in order to create a saturated atmosphere. The resulting solid was analyzed by X-Ray diffraction without further treatment. Form H could also be converted to Form D by drying under vacuum overnight.

Example 17

Preparation of Pravastatin Sodium Form H1

Pravastatin sodium Form Hi was prepared by suspending about 0.5 to 1.4 g of Form D in about 0.6 ml methanol overnight at room temperature, in a sealed 1.10 ml bottle with a sealed cap and a magnetic stirrer The resulting solid was analyzed by X-ray diffraction analysis without further treatment.

Example 18

Preparation of Pravastatin Sodium Form I

Pravastatin sodium Form I was prepared by treating Form D or F with isopropyl vapors for three weeks at room temperature. The procedure was as follows. A 100-200 g sample of pravastatin sodium Form D or F was kept in a 10 ml open glass bottle. The open bottle was introduced into a larger bottle containing few ml of isopropyl alcohol. The larger bottle was sealed in order to create a saturated atmosphere. The resulting solid was analyzed by X-Ray diffraction analysis without further treatment. Form I could also be transformed to Form D by drying under vacuum overnight.

Example 19

Preparation of Pravastatin Sodium Form J

Pravastatin sodium Form J was prepared by treating Form D or F with butanol vapors for three weeks at room temperature. The procedure was as follows. A 100-200 g sample of pravastatin sodium Form D or F was kept in a 10 ml open glass bottle. The open bottle was introduced into a larger bottle containing few ml of butanol. The larger bottle was sealed in order to create a saturated atmosphere. The resulting solid was analyzed by X-Ray diffraction analysis without further treatment. Form J could also be transformed to Form D by drying under vacuum overnight.

Example 20

Preparation of Pravastatin Sodium Form K

Pravastatin sodium Form K was obtained by suspending 0.8 g pravastatin in about 2 ml ethanol and stirring overnight at RT. The resulting solid was analyzed by X-Ray diffraction analysis without further treatment.

Example 21

Preparation of Pravastatin Sodium Form D

Pravastatin sodium (about 100 mg) of any polymorph beside Forms B or D was kept in an oven at 120° C. for 2 hours. The powder was then analyzed by X-ray diffraction and found to be Form D.

Example 22

Preparation of Pravastatin Sodium Form C

Pravastatin sodium was exposed at 100% relative humidity for one week. The power was then analyzed by X-ray diffraction without further treatment and was found to be Form C.

Example 23

Preparation of Pravastatin Sodium Form L and Form D

A solution was prepared, containing 80 kg pravastatin sodium and 144 kg water. The pH of the solution was set to 7.2, by IRC-50 weakly acidic cation exchange resin. Acetone (320 L) was added to the solution and it was treated with 0.8 kg charcol to decolorize. The charcoal was filtered with a solution of acetone:water, 10:1 (176 L). The solution was warmed to 40° C. Acetone (176 L) was added to the solution. The mixture is cooled at a rate of 2° C./h$^{-1}$ rate. The solution is seeded at 32° C. by 0.1% (0.08 kg) pravastatin sodium (Form D). The mixture was cooled to 2° C. and stirred for 2-4 hour.

Pravastatin crystals were filtered and washed with 160 L acetone containing 2% water and cooled to between 2-5° C. Then the wet cake was washed once more with 160 L of pure acetone. The product was dried under vacuum by gradual heating to 60° C. The crystals were identified by X-ray diffraction as Form L. The water content was 16.8% and the acetone content was 0%. After prolonged drying the water content was reduced to 10.7%. A mixture of Form L and D was identified. Further drying reduced the water content to 2.5% water content and the pravastatin sodium was transformed to pure Form D.

We claim:

1. A pharmaceutical composition comprising a crystalline pravastatin sodium or hydrate thereof comprising an X-ray powder diffraction pattern comprising characteristic peaks at 3.6, 6.1, 6.6, 9.0, 9.6, 10.1, 16.4, 16.8, and 18.6±0.2 degrees measured at reflection angle 2θ and a pharmaceutically acceptable carrier, wherein the pharmaceutical composition has a coating.

2. A pharmaceutical composition of claim 1, wherein the coating comprises at least one material selected from the group consisting of phthalic acid cellulose acetate, hydroxypropylmethyl cellulose phthalate, a polyvinyl alcohol phthalic, carboxymethylethylcellulose, a copolymer of styrene and maleic acid, a copolymer of methacrylic acid, methyl methacrylate and mixtures thereof.

3. A pharmaceutical composition of claim 1, wherein the coating is an enteric coating.

4. A pharmaceutical composition of claim 1, wherein the pharmaceutical composition is selected from a dosage form selected from the group consisting of granules, aggregates, a tablet, a capsule, a powder, or combination.

5. A pharmaceutical composition of claim 4, wherein the pharmaceutical composition is an oral dosage form and contains from about 10 mg to about 40 mg of pravastatin sodium.

* * * * *